(12) United States Patent
Vrontakis

(10) Patent No.: US 6,414,220 B1
(45) Date of Patent: Jul. 2, 2002

(54) GALANIN TRANSGENIC MICE

(75) Inventor: Maria E. Vrontakis, Winnipeg (CA)

(73) Assignee: The University of Manitoba, Winnipeg (CA)

( * ) Notice: Subject to any disclaimer, the term of this patent is extended or adjusted under 35 U.S.C. 154(b) by 0 days.

(21) Appl. No.: 09/618,877

(22) Filed: Jul. 19, 2000

Related U.S. Application Data

(63) Continuation of application No. 09/215,051, filed on Dec. 17, 1998, now abandoned.
(60) Provisional application No. 60/069,929, filed on Dec. 17, 1997.

(51) Int. Cl.[7] ..................... A01K 67/00; A01K 67/027; A01K 67/033; C12N 15/00; C12N 15/63
(52) U.S. Cl. ................ 800/18; 435/320.1; 800/13; 800/14; 800/21; 800/25
(58) Field of Search ............... 435/320.1; 800/3, 800/13, 14, 18, 21, 25

(56) References Cited

PUBLICATIONS

Hohmann et al. Transgenic mice that overexpress the galanin gene in brainstem neurons. Society for Neuroscience Abstracts. 23(2): 1878, Oct. 1997.*

Kaplan et al. Tissue–specific expression of the rat galanin gene. Proc. Natl. Acad. Sci. USA 85: 1065–1069, Feb. 1988.*

Wall, RJ Transgenic livestock: Progress and prospects for the future. Theriogenology 45: 57–68, 1996.*

Hammer et al. Spontaneous inflammatory disease in transgenic rats expressing HLA–B27 and human b2m: An animal model of HLA–B27–associated disorders. Cell 63: 1099–1112, Nov. 1990.*

Mullins et al. Fulminant hypertension in transgenic rats harbouring the mouse Ren–2 gene. Nature 344: 541–544, Apr. 1990.*

Mullins et al. Expression of the DBA/2J Ren–2 gene in the adrenal gland of transgenic mice. EMBO J. 8(13): 4065–4072, 1989.*

Taurog et al. HLA–B27 in inbred and non–inbred transgenic mice. J. of Immunol. 141: 4020–4023, Oct. 1997.*

* cited by examiner

*Primary Examiner*—Deborah J. R. Clark
*Assistant Examiner*—Anne-Marie Baker
(74) *Attorney, Agent, or Firm*—Kohn & Associates

(57) ABSTRACT

A transgenic mammal whose somatic and germ cells having a nucleic acid construct wherein the construct includes a mammalian promoter operably linked to a cDNA genomic sequence is provided for the overexpression of galanin. Also provided is a construct having cDNA for the overexpression of galanin. A method of making a transgenic mammal by producing a mammal having a construct for the overexpression of galanin is provided.

5 Claims, 11 Drawing Sheets

| | Transgenic Male | Transgenic Female |
|---|---|---|
| GAL | 1344 ± 88 pg/ml | 628 ± 124 pg/ml |
| GH | 135 ± 14 ng/ml | 120 ± 11 ng/ml |
| PRL | 21 ± 3.1 ng/ml | 17 ± 3.9 ng/ml |
| | Non-transgenic Male | Non-transgenic Female |
| GAL | 150 ± 105 pg/ml | 136 ± 100 pg/ml |
| GH | 82 ± 15 ng/ml | 73 ± 14 ng/ml |
| PRL | 2.4 ± 3.7 ng/ml | 4.0 ± 3.7 ng/ml |
*Figure 3B*
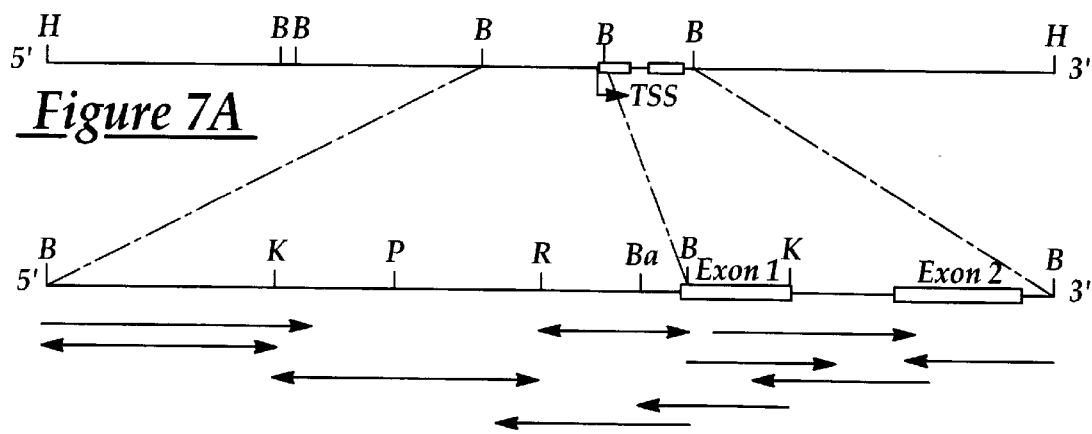
*Figure 7A*
*Figure 7B*
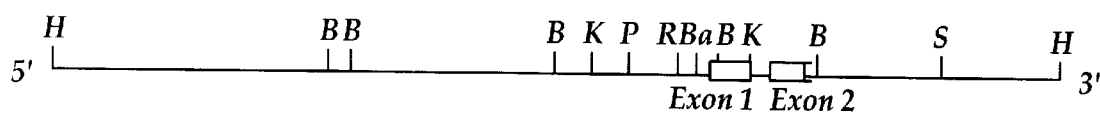
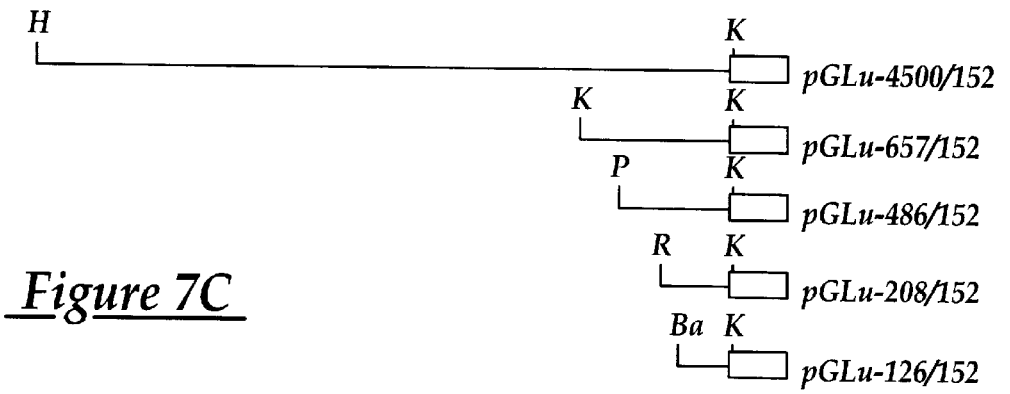
*Figure 7C*

*Figure 6A*
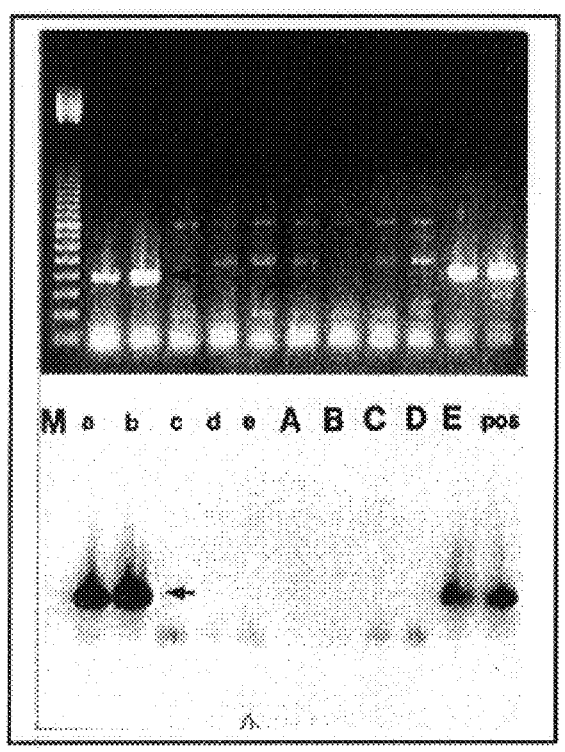
*Figure 6B*
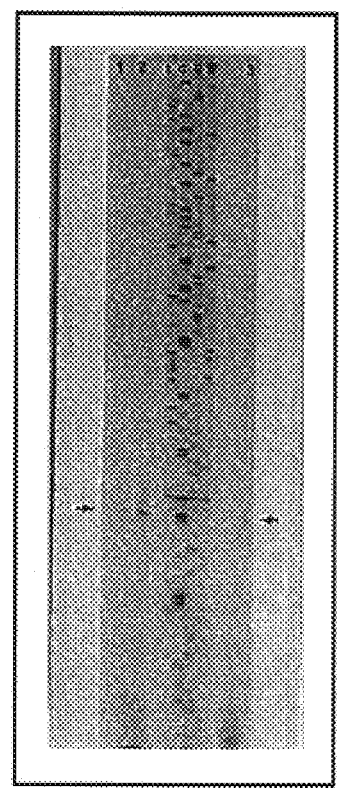
*Figure 6C*

```
-1005                                              ggatc ccagatgggt cttaggagaa gaggggggaca  acttggctca
                                                        GATA
 -960  gggtcatgca gtgttcatca ggacattggt tagcccgagt gactgtggtc tcttgtgatc cgctgctcct  tgctccagca
       ERE1/2
 -880  acggagtcat gttaagccgt gatcagaacc ctcttgggtg aacaaggctc ctcaggacct ggtgtcaccat gctagtgggg
         AP-1                                                              AP-1, ERE ½
 -800  ttcacttctg ggccaggtga cagagtgctc ctgatgagcc ccaaaggcta acacgttcat cagagctgcg ccctggttaa
                       AP-1          GATA
 -720  atatctcacg ctttgggagt ccggagttgc tagctctgtg tctgtcctga ggtgagattt cagggtacct gtatgctgat
       GATA                                                                              GATA
 -640  gtgctgctcc tgcacaggtt ggctaaactc cctgggtgca gacagctctg cacctttggca agaatctggc ctggggctct
                                                                                GATA
 -560  gcaggactca accacagtca cgacagagac cactccagaa acggggctct aagggaaaat ggatggttgg ggcacagctg -480  ccagccaccc tctacccagc cctcagccct gaatggctgc acccctcccc cttttccccc agcaaaagag gaatggagga
                      SP1
 -400  ccctggacca gggtagggaa gctgcagtaa catggtgcaa agcagtcctg ggaatttggt ttctcaggag gtgtccgtga -320  ctggccttgc ttgggctttg gggtggtcca ttccagcccc agccctggga aggagagcaa gacctcctcg ccagcctcag -240  gatgggggtg tcggggacta attcttgtgt gagtacgggg cagaacagtg ggaagtgact ctgtgatgca gggttggccg
       GATA                                                                AP-1
 -160  ggagatagtc tgggactgtg ggtggtcctc tcctgagccc caggagcggg agcgggttcc ggtcacagcg gcccttggga
       GATA                                                                 cEts  ERE ½
 -80   ctcgcaggag gcggcgctga gcgggtgacg cggcagctcc caccgggtat aaatagcggc agcagcgcgg ctcctgcggc
           SP1                  CREB ½                        TATA box
 +1    GGACACGTCG AGGGATCCTC GTGCGCTTCC CTACGCCGCT GATCTGCGCC

+51   ATGCAGTGAG CGACCCTCGC GCCCGCCACT CTACGCCACG CCTGGACGGA

+101   GACACTTGGA CCTGCACTAA CCAGCTACGC CCGGTTCCCA CCACTGCTCA
            Nkx-2
+151   AGgtacccgc gtccaccga ggcttgcctg gccctagtcc tcctgcggtt tgtagcccca tccctgcccc tgcacccctc
                                                                      GATA   SP1
+231   acagtctgt tcccatcacc cagccactcc catgccaatg ccttcgcagt ccaagtgccc cagacatgtg cgtgtgcagg
                GATA      SP1                                       NKx-2
+311   actgctcagg tgcgtccact catccacttc tttccttcca gATGGC CAGG GGCAGCGTTA TCCTGCTAGC
                                                       GATA                       GATA
+381   CTGGCTCCTG TTGGTTGCAA CCCTGTCAGC CACTCTGGGG CTCGGGATGC
                                                                             GATA
+431   CAgtaagtac tggggacagc tgacttgtaa agagggctaa gggtgtcaga tctgaagatc agcctggaag aaggatggtt
                                                  AP-4
+511   cattgtcccc atagcaggaa tagggtgggg ggacatgtcc ctgaagctgc tggagggtgg ggaggatcc
```

*Figure 8*

GALANIN TRANSGENIC MICE

CROSS REFERENCE TO RELATED APPLICATIONS

This application is a continuation of U.S. patent application Ser. No. 09/215,051, filed Dec. 17, 1998, now abandoned, which claims the benefit of priority under 35 U.S.C. Section 119(e) of United States Provisional Patent Application Ser. No. 60/069,929, filed Dec. 17, 1997, which is incorporated herein by reference.

TECHNICAL FIELD

The present invention relates to the production and use of transgenic animal models resulting from overexpression of galanin.

BACKGROUND OF THE INVENTION

The background of U.S. Pat. No. 5,756,460 to Evans, et al. discusses galanin. Galanin is a putative neuropeptide which was first isolated from porcine small intestine in 1983. Porcine galanin is a peptide of 29 amino acid residues which was named for its N-terminal glycine and amidated C-terminal alanine residues. The cDNAs encoding galanin have been cloned from several species including: rat, porcine and bovine, revealing that galanin is a proteolytic product of a larger precursor protein known as preprogalanin. Galanin shows 90% homology between the species but little similarity to other known peptides.

Antibodies raised to porcine galanin have allowed the mapping of galanin-like-immunoreactivity (GAL-LI) to discrete regions of the central nervous system (CNS) and throughout the peripheral nervous system (PNS) of several other species, including man.

Immunohistochemical mapping of GAL-LI in the CNS has been performed most intensively in the rat where the highest concentrations have been found in the median eminance and hypothalamus. These results are consistent with more recent in situ hybridization studies where the localization of preprogalanin in the rat brain tentatively suggests the involvement of galanin in the feeding regulation of several factors ranging from water balance behaviour to blood pressure control. Similarly, radioimmunoassay of galanin in the baboon brain showed high GAL-LI in the hypothalamus and median eminance, and also GAL-LI in association with limbic structures such as the amygdala.

Immunohistochemistry and in situ studies of preprogalanin mRNA during development of the rat has shown tissue specific sex difference in galanin concentration, notably in the anterior pituitary where its expression is estrogen dependent. The overall distribution of GAL-LI and its colocalisation in discrete neuronal cells with catecholamines, scrotonin, GABA, acetylcholine and various other peptides strongly suggest a modulatory role for galanin.

A noteworthy example is the coexistence of galanin with acetylcholine in nerve fibers projecting from the basal forebrain to the hippocampus in the rat and baboon which has led to speculation that galanin may play a role in Alzheimers disease. There is, however, conflicting evidence concerning the expression of galanin in this region of the human brain.

Although the physiological role of galanin in the CNS has not yet been established its pharmacology suggests a role in neuroendocine regulation. Injection of galanin into the third ventricle of rats causes increased growth hormone and injection into the paraventricular nucleus (PVP) enhances food intake.

In the PNS, distribution of GAL-LI suggests that galanin is widespread. Galanin distribution and its pharmacology, which is diverse and often species specific, both suggest a range of physiological actions for galanin. However, some confusion may have arisen as to its pharmacological role through the use of porcine galanin in experiments involving other species.

In numerous mammalian species the highest concentrations of GAL-LI are found in the intestine, pancreas, adrenal glands, and respiratory and genitourinary tracts. Galanin action on the pancreas and its possible role in diabetes is controversial; it has been established that porcine galanin infusion in dogs, and rat and porcine galanin perfusion through the isolated rat pancreas, decrease plasma insulin levels. However, there are conflicting results concerning porcine galanin action on the pig pancreas.

In the dog, galanin also decreases somatoslatin while increasing glucagon but this may not be the case in other species.

Intravenous porcine galanin causes growth hormone secretion in a variety of species including man. However, intravenous porcine galanin infusion in man at a concentration sufficiently high to elicit an increase in growth hormone levels, does not cause the expected inhibition of insulin.

The apparent discrepancy may be due to the difference in amino acid sequence of human versus porcine galanin, or it may be simply a reflection of the species specific effects of galanin. Visualization of GAL-LI in neurons innervating the islets of several species adding to a proposal to explain the galanin induced inhibition of insulin secretion in rat B-cell lines support a neuromoclaistory role for galanin on endocrine pancreatic action. Other pharmacological effects of galanin in the PNS include the species specific stimulatory or inhibitory action of galanin on the smooth muscle activity of several mammalian species.

Galanin receptors have been identified in a hamster insulin-secreting B-cell tumor, rat and monkey brain, and smooth muscle membranes. The distribution of galanin binding correlates with that of GAL-LI and therefore supports the role of galanin in neurotransmission. It is not clear whether there are subtypes of the galanin receptor, nor which region of the peptide is responsible for binding to its receptor. Studies on the biological effect of tryptic fragments of galanin on smooth muscle preparations, in addition to auto-radiographic binding studies on Rin, 5 mf pancreatic B cell lines and on intestinal membrane preparations, present conflicting results.

The molecular biology of the galanin gene has not yet been examined in humans. Porcine preprogalanin is a 23 amino acid residue protein that comprises a signal sequence, galanin (29 amino acids) and a 59 amino acid peptide known as galanin mRNA associated peptide (GMAP). The length and structure of rat porcine and bovine preprogalanin are similar. The 20% difference in galanin amino acid homology across the species is manifest over the C-terminal end of the peptide. The sequence in all species identified to date suggests post translational cleavage of glycine extended galanin followed by amidation. GMAP is also well conserved across the species which has led to speculation that it is biologically active; it includes a region of 35 amino acids that shows 78% homology across the species and within this region a stretch of 17 residues that shows greater homology.

Galanin is widely distributed in the central and peripheral nervous system (Merchenthaler, et al., (1993); Vrontakis, et al., (1991)), and most abundantly in the hypothalamus where it may serve in the regulation of anterior pituitary hormones (Vrontakis, et al., (1991); Ottlez, et al., (1988)). In vitro studies have shown that galanin may regulate hormone secretion directly at the level of the pituitary gland (Gabriel, et al., (1988); Wynick, et al., (1993)). Central administration of galanin results in increased plasma levels of GH and PRL in a dose dependent manner (Murakami, et al., (1989); Koshiyama, et al., (1987)).

It has previously been demonstrated that galanin is dramatically upregulated by estrogen in the anterior pituitary (Vrontakis, et al., (1989); Kaplan L M et al., (1988)), primarily within the somatotrophs and lactotrophs (Steed J et al., (1989); Hyde J F, et al.). A correlation between the development of pituitary hyperplasia and the increase of galanin mRNA and peptide concentration exists, indicating that galanin might act as a mitogen in the formation of pituitary adenomas (Vrontakis M E et al, (1987); Moore J, et al., (1994); Leile V, et al., (1993)). Similarly axotomy of sensory or motor neurons dramatically increases galanin mRNA and protein (Rutherford S D, et al., (1992); Mohney R P, et al., (1994)). It has been proposed that these changes in peptide expression could be related to unknown trophic mechanisms of importance for survival and regeneration.

It would therefore be useful to have transgenic models which show the overexpresion of galanin

SUMMARY OF THE INVENTION

According to the present invention, a transgenic mammal whose somatic and germ cells having a nucleic acid construct wherein the construct includes a mammalian promoter operably linked to a cDNA genomic sequence for the overexpression of galanin is provided. Also provided is a construct having cDNA for the overexpression of galanin. A method of making a transgenic mammal by producing a mammal having a construct for the overexpression of galanin is provided.

DESCRIPTION OF THE DRAWINGS

Other advantages of the present invention will be readily appreciated as the same becomes better understood by reference to the following detailed description when considered in connection with the accompanying drawings wherein:

FIG. 3b) shows a table of serum levels for Galanin, Growth Hormone and Prolactin. Values=Mean±SEM;

FIGS. 6A–6C show the results of PCR screening and primer extension; Panel A shows the ethidium bromide staining of PCR products; Panel B shows the hybridization to rat galanin specific oligonucleotide; the templates for each reaction were: lane M, marker; lanes a–e, pools of rows; lanes A–B, pools of columns; lane pos, 20 ng rat genomic DNA, the arrows denote the positive PCR products; Panel C shows a determination of the transcriptional start site of the rat gelanin gene by primer extension analysis, about 10 μl of total RNA were hybridized to the $^{32}$P-labelled oligonucleotides and then extended by the MMLV reverse transcriptase; lane 1, total RNA isolated from rat pituitary; lane 2, total RNA isolated from estrogen treated rat pituitary; lane t,c,g,a, sequence using the same $^{32}$P-labelled oligonucleotides as primer; lane 3, total RNA isolated from rat uterus, the main extended products are indicated by arrows;

FIGS. 7A–7C show a mapping of the clone and the deletion constructs; Panel A shows the restriction enzyme analysis of the 8 kb-Hind III fragment of the rat galanin gene clone with Hind III and Bam HI, TSS is the transcription start site; Panel B shows further restriction enzyme analysis of portions of the 8 kb-Hind III fragment and the sequence strategy after subcloning into the pGEM-7Z, the extent and direction of the sequencing is indicated with arrows under the restriction map; enzyme abbreviations are as follows: B, Bam HI; Ba, Ban II; H, Hind III; K, Kpn I; P, Pvu II; R, Rsa I; Panel C shows the deletion constructs and their locations in the rat galanin gene;

FIG. 8 shows the nucleotide sequence (SEQ. ID. NO. 8) of the proximal rat gelanin gene promoter and its exon 1, exon 2 and the first intron, a TATA-like box and consensus sequences for known protein binding factors are indicated in bold or underlin, ERE, estrogen receptor comples; CREB, mediating the response to cAMP and/or calcium; GATA, zinc finger transcription factor; AP-1, TPA response element; consensus sequence for other response elements as indicated;

DETAILED DESCRIPTION OF THE INVENTION

Figure 1A:
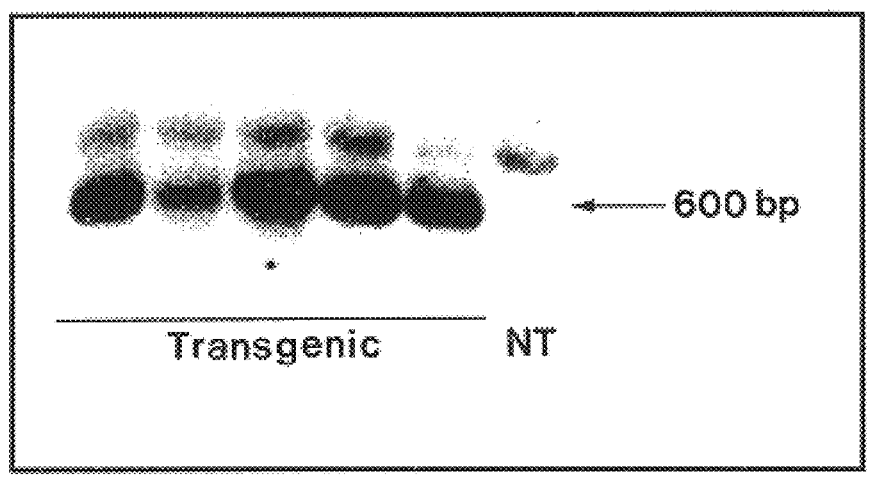
FIG. 1 shows a (A) Southern blot hybridization of tail DNA. (B) Northern blot analysis of individual pituitary total RNA.

The present invention provides a method of producing transgenic animals with a modulated phenotype from the original/initial transgenic animals. The modulation can be either an enhancement of the original observed phenotype seen in the original transgenic animals or a diminution of the phenotype. By modulation, it is meant that the characteristic phenotype shown by the transgene is more pronounced; where galanin is expressed more than is found in the parent strains.

More specifically, the present invention provides a construct (Seq ID No:1–4) for the generation of transgenic mice that overexpresss galanin in the pituitary and secrete (oversecrete) the galanin into the serum having significantly higher levels than nontrangenic animals. These mice also have a high rate of lymphoma which links galanin as a growth factor causing the development of lymphoma. The mice also have high levels (overexpression) of growth hormone and prolactin serum levels. The present invention also provides transgenic mice carrying the transcript and their offspring as well as cell lines derived from the transgenic mice. The present invention further provides for the use of the galanin transgenic mice in a model to test pharmacological and therapeutic efficacy of drugs in dementia and cognitive disorders and in neuronal injury, nerve regeneration and neuropathic pain.

In general, where the transgene carries a mutation, it is referred to by the mutation. The mutation is abbreviated by the non-mutant amino acid followed by the location in the sequence followed by the substituted amino acid.

The transgene generally is a human gene where a human condition is being studied. The transgene (generally in the form of cDNA) can be the nonmutant (often referred to as "wildtype") or a mutant human gene. Additionally, a non-mutant transgene can also be treated as is known in the art to express mutations.

Cells can be isolated from the offspring which carry a transgene from each transgenic mammal and that are used to establish primary cell cultures or cell lines as is known in the art.

Where appropriate, a mammal strain will be homozygous for the transgene. Additionally, where appropriate, the endogenous nontransgene in the genome that is homologous to the transgene will be nonexpressive. By nonexpressive is meant that the endogenous gene will not be expressed and that this nonexpression is heritable in the offspring. For example, the endogenous homologous gene could be "knocked-out" by methods known in the art. Alternatively, the mammal strain that receives one of the transgenes could carry a mutation at the endogenous homologous gene rendering it nonexpressed.

The transgenic mammals are produced as is known in the art. The present invention provides for transgenic mammal strains containing transgenes as described herein above and including gene targeted or overexpressed mutant or nonmutant transgenes and where appropriate as well as for knock-out strains carrying a transgene. Any method can be used which provides for stable, inheritable, expressible incorporation of the transgene within the nuclear DNA of an animal. These transgenic animals are constructed using standard methods known in the art and as set forth in U.S. Pat. Nos. 5,614,396 5,487,992, 5,464,764, 5,387,742, 5,347,075, 5,298,422, 5,288,846, 5,221,778, 5,175,384, 5,175,383, 4,873,191, 4,736,866 as well as Burke and Olson [1991], Capecchi [1989], Davies et al. [1992], Dickinson et al. [1993], Duff and Lincoln [1995], Huxley et al. [1991], Jakobovits et al. [1993], Lamb et al. [1993], Pearson and Choi [1993], Rothstein [1991], Schedl et al. [1993], Strauss et al. [1993]. Further, patent applications WO 94/23049, WO 93/14200, WO 94/06908, WO 94/28123 also provide information.

More specifically, any techniques known in the art may be used to introduce the transgene expressibly into animals to produce the mammal lines of animals. Such techniques include, but are not limited to, pronuclear microinjection (U.S. Pat. No. 4,873,191); retrovirus mediated gene transfer into germ lines [Van der Putten et al., 1985]; gene targeting in embryonic stem cells [Thompson et al., 1989 and U.S. Pat. No. 5,614,396]; electroporation of embryos [Lo, 1983]; and sperm-mediated gene transfer [Lavitrano et al., 1989]. For a review of such techniques'see Gordon [1989].

A description of the construct is set forth herein. The construct can have rat, human or other species cDNA for galanin. The transgenic animal carrying the construct can be a knockout for the homologous galatin gene. The promoter specifically targets galanin to somatotrophs which provides the successful expression of the gene. Other groups have used promoters that target lactotrophs and have not been successful. The choice of the tail of the construct was made to allow for intergration of the transgene.

The above discussion provides a factual basis for the use of transgenic mammal having a construct for the overexpression of galanin. The methods used with and the utility of the present invention can be shown by the following non-limiting examples and accompanying figures.

EXAMPLES

General Methods

General Methods in Molecular Biology:

Standard molecular biology techniques known in the art and not specifically described are generally followed as in Sambrook et al., *Molecular Cloning: A Laboratory Manual*, Cold Springs Harbor Laboratory, New York (1989, 1992), and in Ausubel et al., *Current Protocols in Molecular Biology*, John Wiley and Sons, Baltimore, Md. (1989). Polymerase chain reaction (PCR) is carried out generally as in *PCR Protocols: A Guide To Methods And Applications*, Academic Press, San Diego, Calif. (1990). Reactions and manipulations involving other nucleic acid techniques, unless stated otherwise, are performed as generally described in Sambrook et al., 1989, *Molecular Cloning: A Laboratory Manual*, Cold Spring Harbor Laboratory Press, and methodology as set forth in U.S. Pat. Nos. 4,666,828; 4,683,202; 4,801,531; 5,192,659 and 5,272,057 and incorporated herein by reference. In-situ (In-cell) PCR in combination with Flow Cytometry can be used for detection of cells containing specific DNA and mRNA sequences (Testoni et al, 1996, Blood 87:3822.)

General methods in immunology: Standard methods in immunology known in the art and not specifically described are generally followed as in Stites et al. (eds), *Basic and Clinical Immunology* (8th Edition), Appleton & Lange, Norwalk, Conn. (1994) and Mishell and Shiigi (eds), *Selected Methods in Cellular Immunology*, W. H. Freeman and Co., New York (1980).

In general, ELISAs are the preferred immunoassays employed to assess a specimen. ELISA assays are well known to those skilled in the art. Both polyclonal and monoclonal antibodies can be used in the assays. Where appropriate other immunoassays, such as radioimmunoassays (RIA) can be used as are known to those in the art.

Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, *Molecular Cloning: A Laboratory Manual*, Cold Springs Harbor, N.Y., 1989

Transgenic and Knockout Methods

The present invention provides for transgenic gene and polymorphic gene animal and cellular (cell lines) models as well as for knockout models. These models are constructed using standard methods known in the art and as set forth in U.S. Pat. Nos. 5,487,992, 5,464,764, 5,387,742, 5,360,735, 5,347,075, 5,298,422, 5,288,846, 5,221,778, 5,175,385, 5,175,384, 5,175,383, 4,736,866 as well as Burke and Olson (1991), Capecchi (1989), Davies et al. (1992), Dickinson et al. (1993), Duff and Lincoln (1995), Huxley et al. (1991), Jakobovits et al. (1993), Lamb et al. (1993), Pearson and Choi (1993) Rothstein (1991), Schedl et al. (1993), Strauss et al. (1993). Further, patent applications WO 94/23049, WO 93/14200, WO 94/06908, WO 94/28123 also provide information.

Example 1

The rat galanin cDNA has been isolated and characterized from a pituitary tumor library. (JBC1987)

A transgenic mouse has been created where the rat galanin cDNA has been specifically targeted to the anterior pituitary. Three independent lines have been developed. In these mice galanin is over expressed and over secreted with the galanin serum levels 10 times higher in transgenics compared to non transgenics. Transgenic mice exhibit infertility problems while homozygous mice are not compatible with life. In these mice anterior pituitary function is significantly affected including proliferation of somatotroph and lactotroph cells, giving direct causal evidence for the growth promoting effects of galanin.

The high serum levels of galanin in the transgenic model makes it a unique tool to study the involvement of galanin in two important and very demanding areas of research. 1) Alzheimer's disease and/or other dementia 2) Axonal nerve regeneration.

1) There is increasing evidence that galanin affects learning and memory in rats while in humans galanin is the only neuropeptide that is increased in postmortem brains of Alzheimer's patients. Data has been obtained using the food reward T-maze that the transgenic animals have impaired memory.

2) Galanin is dramatically upregulated following neuronal injury. It has been speculated that genes (or proteins) that are important for survival and regeneration are the ones that are upregulated. Results (both morphological and functional) in the present model, where galanin is already over secreted with serum levels ten times higher than non-transgenics, the recovery of sciatic nerve injury is much faster.

The Galanin Transgene.

r.GH-r.Galanin cDNA construct

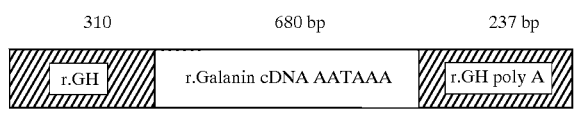

The rat GH promoter with the BamHI modified site at position (+7) to XhoI was used. The 320 bp KpnI/XhoI fragment was isolated the XhoI site was filled in and the KpnI/XhoI blunt fragment was inserted in the KpnI/Sma site of the PUC 119 vector. The poly A tail of the rat GH gene was obtained by digesting the PvuII sites of the 5.8 Kb gene and isolating the 237 bp fragment. This PvuII/PvuII fragment was inserted in the Xba/blunt site of the KpnI/SmaI GH/PUC119 construct and the right orientation was chosen by checking the PstI fragments of the transformants. Finally the EcoRI fragment of our Rat Galanin cDNA fragment (M. Vrontakis et al. JBC 1987) was blunted by filling in with Klenow and inserted in the blunt BamHI site of the KpnI/XhoI GH/ PvuII/PvuII GH/PUC119 vector. The right orientation of the transformant was checked by sequencing both sides of the construct with T3 and T7 primers. The transgene was removed by EcoRI/HindIII digestion.

Example 2

In vitro studies have shown that galanin may regulate hormone secretion directly at the level of the pituitary gland (Gabriel S M, et al., (1988); Wynick D., et al., (1993)). Central administration of galanin results in increased plasma levels of GH and PRL in a dose dependent manner (Murakami Y et al., (1989); Koshiyama H. et al., (1987)). It has previously been demonstrated that, galanin is dramatically upregulated by estrogen in the anterior pituitary (Vrontakis M E et al., (1989); Kaplan L M et al., (1988)), primarily within the somatotrophs and lactotrophs (Steed J et al., (1989); Hyde J F, et al.).

A correlation between the development of pituitary hyperplasia and the increase of galanin mRNA and peptide concentration exists, indicating that galanin might act as a mitogen in the formation of pituitary adenomas (Vrontakis M E et al, (1987); Moore J, et al., (1994); Leile V, et al., (1993)). Similarly axotomy of sensory or motor neurons dramatically increases galanin mRNA and protein (Rutherford S D, et al., (1992); Mohney R P, et al., (1994)). These changes in peptide expression are related to unknown trophic mechanisms of importance for survival and regeneration. Mice carrying rat galanin cDNA specifically targeted to somatomammotrophs under the control of the rate GH promoter, overexpress and oversecrete galanin. Somatotroph and lactotroph cell hormone release seems to be increased as well while after six months of age transgenic animals develop pituitary adenomas. Transgenic mice exhibit infertility problems and homozygous mice are not compatible with life. Finally, 3–10% of transgenic mice from all three lines develop lymphomas. Galanin is acting as a trophic factor involved in the induction of somatomammotroph adenomas and dysfunction of GH and PRL cells.

A construct consisting of the rat GH promoter (−311 to +8) fused to the rat galanin cDNA containing the whole coding region and the poly A tail, was prepared in order to specifically target rat galanin to pituitary somatotrophs in transgenic animals by pronuclear injection in mice embryos. Four founders, all females, were identified.

Lines from each female founder were bred and analyzed by restriction analysis of tail DNA and the identification of specific sized band by Southern Hybridization (FIG. 1A). Out of the four founders one was infertile and subsequently developed lymphoma. Some of the offspring were infertile as well. Despite efforts to establish homozygous lines, it has been unsuccessful, while breeding of heterozygous mice gave birth to smaller numbers of pups (Ottlez A, et al., (1988); Gabriel S M, et al., (1988)) compared to non-transgenic (Steed J et al., (1989); Hyde J F, et al.; Vrontakis M E et al, (1987)) indicating that possibly homozygous transgenics might be embryonically lethal. At different ages (from 3 to 20 months), heterozygous transgenic and non transgenic littermates were sacrificed and their pituitaries removed and either fixed in 10% buffered formalin or frozen for RNA extraction.

Figure 1B:
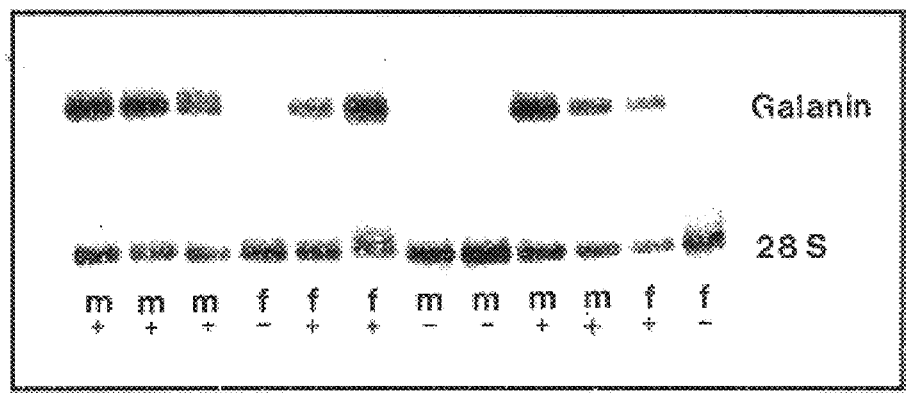

By Northern hybridization, both female and male transgenics overexpressed galanin (FIG. 1B). Sequential hybridization of the same blot with galanin, PRL and GH cDNA probes revealed that in female transgenics all three transcripts were upregulated, while in male transgenics the PRL only and galanin transcript were upregulated. Thus galanin through autocrine and paracrine mechanisms affects the synthesis of both GH and PRL. This is the first demonstration that galanin can affect mRNA levels of GH and PRL.

Figure 2:
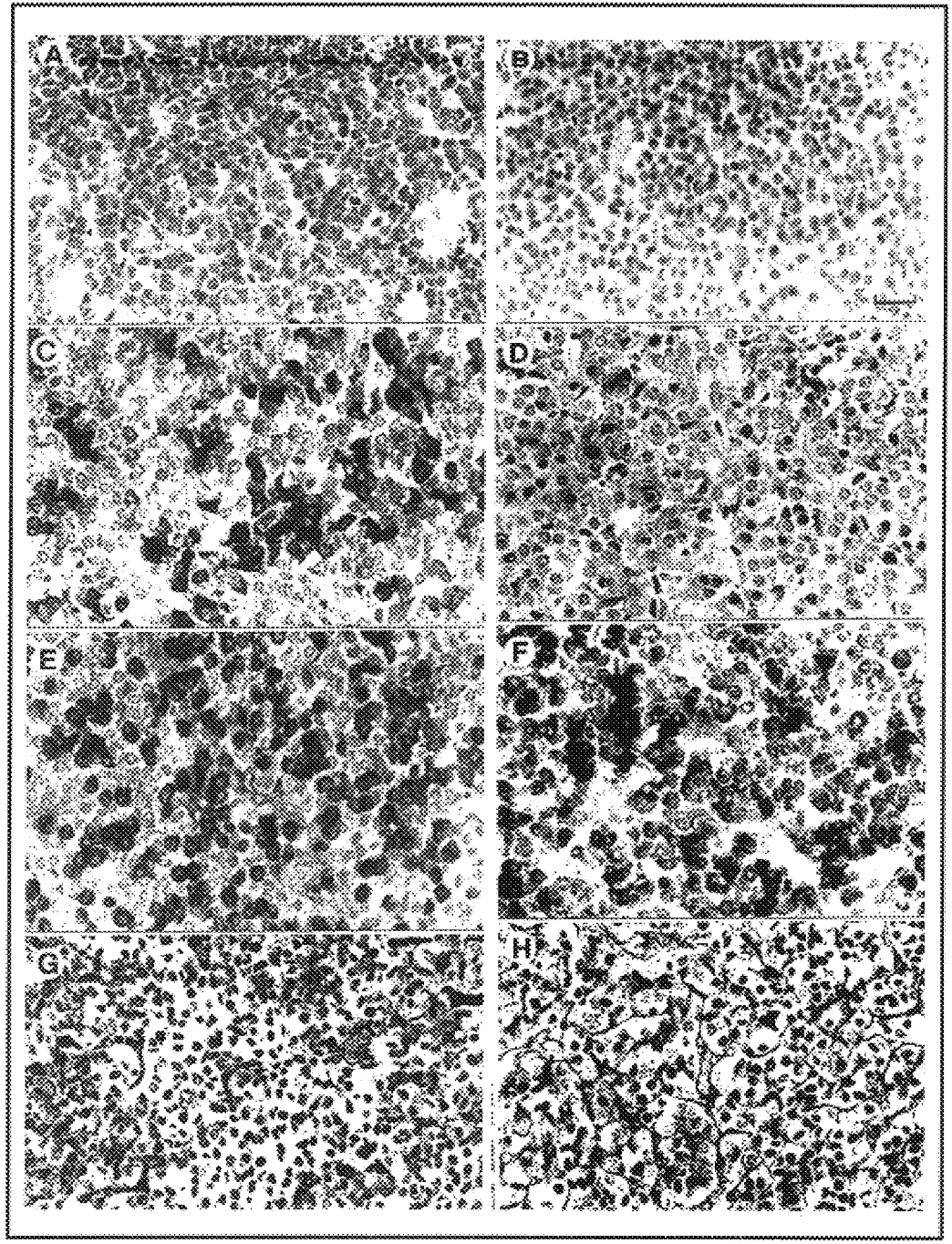
FIGS. 2A–H show transgenic (A,C,E,G) and non-transgenic pituitary sections (B,D,F,H); (A, B) Hemotoxylin-Eosin staining, (C, D) galanin immunostaining, (E,F) Growth Hormone immunostaining, (G,H) Gordon Sweet Silver staining. Bar=1 cm=20 μm.

Formalin fixed, paraffin embedded pituitaries were examined by histology and immunohistochemistry. FIG. 2 shows pituitaries from transgenic and non-transgenic animals. The pituitaries of transgenic mice contained several cells for galanin (FIG. 2C) which were greater in number and density, compared to nontransgenic littermates (FIG. 2D).

Regarding the cell type both GH and PRL cells exhibited galanin staining. Since the rGH promoter was used the transgene initially was targeted to the GH cells. There is enough evidence suggesting that the majority of PRL expressing cells appear to be derived from the GH producing precursor (Karin M et al., (1990)). Complete ablation of somatotrophs by expression of GH-diphtheria toxin and GH-thymidine kinase fusion genes inserted into the gene line of transgenic mice also result in elimination of most of the lactotrophs (Borreli E et al., (1989); Behringer R R, et al., (1988)). These observations support the lineal relationship between somatotrophs and lactotrophs. This can explain the expression of the galanin gene in both somatotrophs and lactotrophs of our transgenics.

Figure 3A:
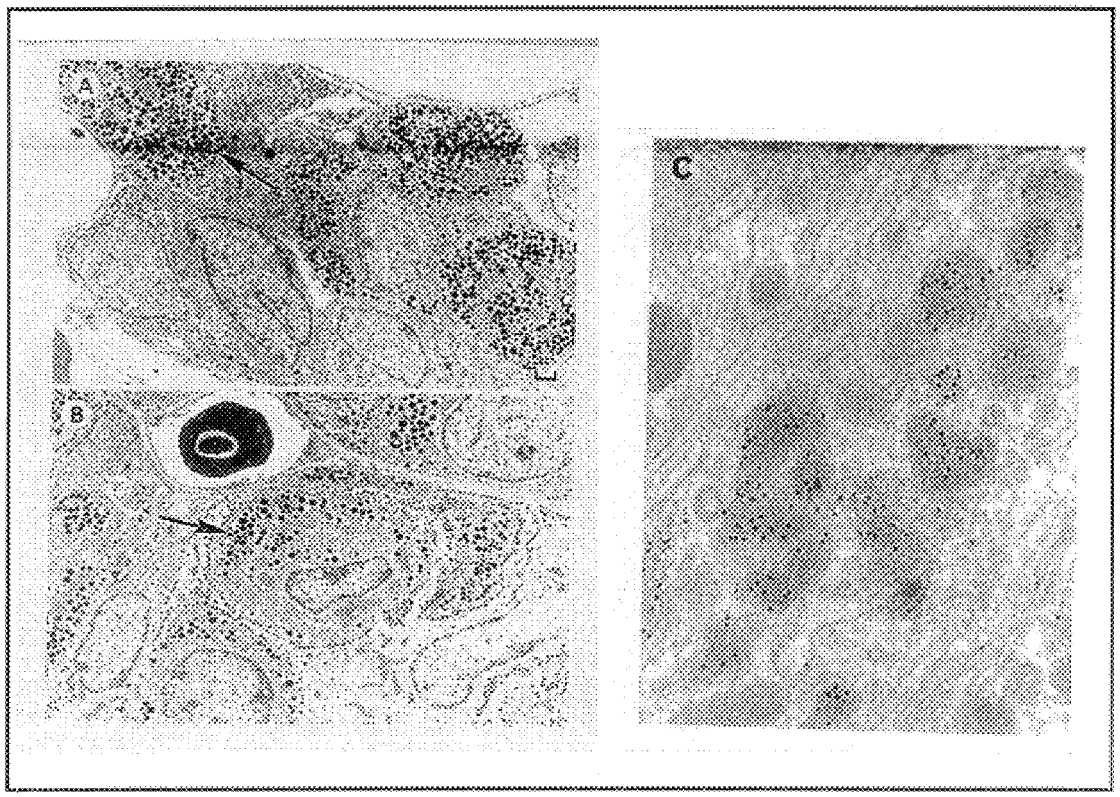
FIG. 3a) shows an electron microscopy of transgenic (A) and non-transgenic (B) pituitary. Bar=1 μm.

Electron microscopy demonstrated more numerous cells with the ultrastructural characteristics of GH cells (FIG. 3A). These cells were densely granulated in transgenics compared to the nontransgenics.

Analysis of serum demonstrated that serum galanin levels were significantly ($p<0.001$) elevated in transgenic animals. There was a sex difference in this elevation with much higher response in males than females ($1344\pm88$ vs $628\pm124$, $p<0.005$). Regarding GH and PRL levels both were significantly elevated in transgenic animals ($p<0.001$). The PRL levels were very well correlated with the Galanin levels, giving a direct evidence of autocrine/paracrine effect of galanin on PRL cell function.

Mice of six months of age and older developed pituitary adenomas, as was demonstrated by total breakdown of the reticulin fiber network (FIG. 2 G,H). This data is in agreement with previous observations suggesting that galanin mRNA levels correlate with tumor formation. In both estrogen induced pituitary tumors and in GHRH transgenic mice pituitary tumors, galanin mRNA levels and protein were closely correlated with the development of these tumors (Vrontakis M E et al, (1987); Moore J, et al., (1994); Leile V, et al., (1993)). The data give direct causal evidence for the growth promoting effects of galanin. Two subtypes of the galanin receptor have been cloned by a number of groups for both the human and the rat (Howard A D, et al., (1997); Sallivon K A, et al., (1997)) sharing 38% homology. Moreover, the Gal $R_2$ receptor is expressed in the anterior pituitary (Howard A D, et al., (1997)).

Severe lymphomas developed in 3–10% of the transgenics in all three lines (FIG. 4), including the two founders. No lymphomas were detected in non-transgenic littermates.

The human galanin gene has been located in chromosomes 11 g 13.3–g 13.5 (Evans H., et al., (1993)). This location is of potential interest as it is the breaking point region for translocation associated with chronic lympholytic leukemia and diffuse B cell lymphoma (Evans H., et al., (1993)). In light of reports that galanin is mitogenic for small cell lung (Sethi T, et al., (1991)) carcinomas, and may play a role in regeneration of injured neurons (Ji R R, et al., (1995); Palkovits M, (1995)) acting as a growth factor, this association requires further analysis.

In summary, it has been shown that overexpression of galanin in GH and PRL cells has a paracrine/autocrine effect on somatotroph and lactotroph function and tumor formation.

Methods

The transgene was constructed using a 320 bp Kpn I/BamHI fragment of the rat GH promoter (−311 to +8) that was the gift from Dr. P. Cattini. This fragment contains the pituitary specific elements and was fused to the rat galanin cDNA (full length) clone including its poly A tail following by the poly A tail of the rat GH gene (Pvu II. 237 bp fragment). The transgene was purified by electroelution from 1% agarose gel followed by CsCI purification. Pronuclear infection of the transgene into mouse embryos were done by DNA (digested with Kpn I/Sal I), Southern hybridization with a GH (Kpn I/BamHI) probe giving rise to a 600 bp fragment.

Animals:

Founders were a C578BL/6×SJL $F_2$ background. For the generation of lines they were crossed with Swiss SW.

Northern Blotting:

Total RNA was prepared from each pituitary individually using the guanidine isothiocyanate method. Hybridization was performed using the rat galanin cDNA probe, rat GH and rat PRL cDNAs (full length), under identical conditions.

Morphology:

Tissues were fixed in 10% neutral buffered formalin and embedded in paraffin. Sections (4–5 mm thick) were stained with Gordon Sweet silver method to demonstrate the reticulin fiber network.

Immunocytochemistry was performed with the avidinbiotin-peroxidase complex technique. The duration of incubation to primary antisera was 24 hours at 4° C. The primary antisera were directed against the following antibodies: Galanin (Peninsula Laboratory) dilution 1:3000. GH and PRL (all donated from the National Hormone and Pituitary Program NIDDK, NICHHD, Bethesela, Md.) diluted 1:2000 and 1:1000, respectively. For EM study, pituitary glands were cut into small pieces and fixed in 3% glutaraldehyde in 0.1M phosphate buffer (pH7.4). After an overnight rinse in 0.1M PBS containing 0.2M sucrose, the tissues were postfixed in 1% osmium tetroxide in 0.1M phosphate buffer for two hours at 4° C., dehydrated in ascending concentrations of ethanol and embedded in Epon 812. Thin sections were stained with uranyl acetate and lead citrate, viewed and photographed in a Philips EM 201 electron microscope.

RIA:

Galanin RIA was performed as previously described (Vrontakis M E, et al., (1992)). For GH, the murine mGH double antibody radioimmunoassay was used with materials provided by Dr. Parlow and according to their protocol. For PRL, mPRL reagents were used for RIA generously supplied by Dr. F. Takamantes, Sinsheimer Laboratories, U of California (Lopez J and Talamantes F, (1983)).

Statistical Analysis:

Serum levels were analyzed using ANOVA. Data are preseeded as Mean±SEM.

Example 3

Galanin is a 29 aminoacid neuropeptide the physiological role of which is still not clear. Preprogalanin mRNA and galanin protein are dramatically induced in the anterior pituitary by estrogen. Galanin has been colocalized in the somatomammotrophs and thyrotrophs of the anterior pituitary. To further elucidate the biological role of galanin in the anterior pituitary, mice transgenic for rat galanin were developed by pronuclear injection of the galanin construct in mice embryos. Transgenic integration was identified by restriction analysis and Southern hybridization of DNA from the tails, at three weeks of age. The galanin construct consisted of the rat galanin cDNA under the control of the rat GH promoter (−310 to +8), provided by Dr. Cattini, that has previously been shown to specifically target the somatomammotroph cell lineage. Four founder animals, all females, were identified. One founder is infertile and so three heterozygous lines have been generated by the other three founders.

Northern analysis of single pituitaries have shown significant overexpression of the galanin gene in the transgenics compared to non transgenic littermates. Formalin fixed, paraffin embedded pituitary glands from three to six month old mice were examined by histology and immuno histochemistry. The pituitaries of transgenic mice contain several strong staining cells for galanin, much higher in number and density, compared to non transgenic littermates that show very little staining for galanin in the anterior pituitary. The three and six month old heterozygous mice examined has revealed no significant pituitary hyperplasia so far.

Female animals expressing the transgene have a significant lower body weight compared to non transgenic littermates. In the contrary, the male animals expressing the transgene have a higher body weight compared to non transgenic controls. Transgenic animals give birth to smaller number of babies compared to controls.

Example 4

Galanin, a biologically active neuroendocrine peptide, may play a role in brain dysfunction in Alzheimer's disease. In rats, administration of galanin inhibits acetylcholine release in the ventral hipocampus and produces deficits in learning and memory tasks. Transgenic mice were generated where galanin is overexpressed and oversecreted in the pituitary, with galanin levels in the circulation 10 times higher in the transgenics compared to non transgenics. To characterize the effects of galanin overexpression and oversecretion on memory processes, transgenic and non transgenic littermates were exposed gradually to five different difficult food reward mazes.

The speed (timing) to reach the reward and the number of errors (blind alleys entered) were monitored. After the training period and where each mouse had achieved its optimal score in two consequent trials, the testing period started, for intervals of three days, four days and one week in the most difficult maze (5th) and the performance task was monitored again. While there were no significant differences in the transgenic and non transgenic performance during the training period, there was a statistically significant difference in both the speed and the number of errors between the two groups during the training period, there was a statistically significant difference in both the speed and the number of errors between the two groups during the testing period (19±3 seconds vs 8±1.2 seconds and 3.5±0.5 errors vs 0.5±0.1 errors), indicating that in the transgenic mice the retrieval of memory or performance rather than the acquisition of memory were affected. Measurement of neurotransmitter levels in different brain regions and the adrenals by HPLC has shown as well statistically significant changes in the levels of NE, indicating that an imbalance in neurotransmitters may contribute to the memory deficits as well.

Example 5

Galanin is strongly upregulated by nerve injury, estrogen and during development by mechanisms largely unknown. A rat genomic clone was isolated by PCR method, containing at least 4.5 kb 5' Flanking sequence. Partial sequence analysis of the clone revealed that the structure of the rat galanin gene is very conserved among species. Similarly to the bovine, human and the mouse genes, the rat gene has several transcriptional factor binding site consensus sequences, including a CREB, 3 half EREs, several GATA, SP1 and AP-1. To locate functionally active regulatory elements of the rat galanin gene plasmids were constructed containing various length of the rat galanin 5' Flanking sequence and the first exon, fused into a promoterless luciferase plasmid. These hybrid genes were transfected into a neuroblastoma (SK—N—MC) cell line, a pheochromocytoma ($PC_{12}$) cell line, a pituitary tumor cell line ($GH_3$) and Hela cells, by transient transfection. Galanin gene was transcriptionally activated in both neuronal and endocrine cell lines while no activity was detected in Hela cells.

The first 200 bp of the galanin promoter contain a strong neuronal tissue specific element and responsive elements to TPA and NGF as well. Strong negative regulatory elements are located upstream of the −657 bp and downstream of the 200 bp as well. Mobility gel shift assay has identified a strong suppressor binding activity and a strong positive binding activity in neuronal cells that is further induced by TPA. Functional neuronal tissue specific elements are present in the proximal region of the rat galanin gene.

Example 6

Galanin-like immunoreactivity (LI) and mRNA are present in a variety of tissues (5–18) including the brain, spinal cord, pituitary, decidua, pancreas, gastrointestinal and genitourinary tract.

Although the physiological role of galanin is not known, it has shown a diversity of biological effects such as inhibition of insulin release (Ahren, et al., (1988); Davis, et al., (1987)), regulation of smooth muscle activity (Bek et al., (1988)), stimulation of growth hormone release (Ottlez, et al., (1988); Murakami, et al., 91987)), inhibition of acetylcholine release (Pramanik, et al., (1993)), neurotransmitter release (Fisone, et al., (1987)), and affection in learning and cognitive functions (Crawley (1993); Ogren, et al., 91992); Crawley, et al., (1989)). Galanin has also been implicated in the pathology of Alzheimer's dementia (Crawley (1996)).

Distinctive feature of galanin gene expression is its dramatic up-regulation by estrogen, primarily in the rat anterior pituitary (Vrontakis, et al., (1989); Kaplan, et al., (1988)). Similarly axotomy of sensory or motor neurons dramatically increases galanin mRNA and protein (Zhang, et al., (1993); Hoekfelt, et al., (1994)). It has been proposed that these changes in peptide expression could be related to unknown trophic mechanism of importance for survival and regeneration.

In summary, the widespread distribution and diverse function of galanin along with its conserved sequences among species suggest that galanin is an important messenger for inter-intra cellular communication within the nervous and endocrine system. The differential regulation of galanin expression in the nervous and endocrine systems suggests that a single gene may be activated by multiple pathways. Therefore, the molecular mechanism of galanin gene activation in different tissues are of particular interest.

To explore the transcriptional activation of the galanin gene and to locate functionally active (tissue and hormonal specific) regulatory elements, the 5' Flanking region of the rat galanin gene was cloned and sequenced.

Materials and Methods
Genomic Library Screening, DNA Isolation and Characterization.

A rat liver genomic DNA library (Strategene, Lambda DASH®vector) was screened using a PCR-based method for high stringency screening (Israel (1993)).

Briefly, the genomic library which was amplified once was subdivided into 25 eppendop tubes, each containing approximately $2 \times 10^5$ phage clones (depended on the frequency of the clones containing the rat galanin gene) and propagated in the bacteria of XL1-Blue MRA (P2). Amplified phage from each five tubes across column or each of five tubes down rows, were pooled (FIG. 1) The matrix of 25 tubes was therefore reduced to ten pools, which were used as templates for PCR analysis using specific oligonucleotide primers complement with the sequence from exon 1 and exon 2 of the rat galanin cDNA (Vrontakis, et al., (1987)). An internal oligonucleotide located between the upper and lower primer in the cDNA sequence was used to examine the PCR products by Southern analysis. Primer sequences were as follows: upper primer (GAL 1) 5'-GCCATGCAGTGAGCGACCC-3' SEQ. ID. NO. 4; lower primer (Gal 2) 5'-GCATCCCGAGCCCCAGAGTG-3' SEQ. ID. NO. 5; internal oligonucleotide 5'-CCTGGACGGAGACACTTGGACCTGC-3' SEQ. ID. NO. 6 which was used as a hybridization probe for the PCR products.

The PCR reaction mixture included 1×PCR buffer/1.5 mM MgCl (Boehringer Mannheim), 0.2 mM dNTP, 0.9U Expand HF PCR System enzyme mix (Boehringer Mannheim), 0.5 µl template (phage stock or purified rat genomic DNA), 25 pmol of each oligonucleotide primer. The PCR reactions first were incubated at 70° C. for five minutes. After on ice for a while, they were performed in a thermal cycler (MiniCycler) with 94° C. for 1.5 minutes, following by 35 cycles of at 94° C. for 30 seconds, 57° C. for 30 seconds, 68° C. for 1.5 minutes, and at 68° C. again for 5 minutes at the end of 35 cycles and held at 4° C. prior to gel analysis.

PCR products were electrophoresed in 1.5% agoras gel and analyzed by Southern blot using end-labelled internal oligonucleotide as a probe in 6×SSC, 12.5×Denhardt's reagent, 0.5% SDS, 200 µg/ml denatured salmon sperm DNA, at 65° C. prehybridization for 1.5 hr and hybridization overnight. The filter was washed at 65° C. in 1×SSC/0.1% SDS.

Plaque filter with immobilized DNA from plaques of the positive tube were performed using the same internal oligonucleotide probe and hybridized and washed as described above.

DNA was prepared from the positive genomic clone after growth in liquid culture purification by DEAE-cellulose column chromatography (Ausubel, et al., eds, (1994)). After restriction enzyme analysis and Southern blot analysis (using internal oligonucleotide probe), an 8 kb-Hind III fragment of bacteriophage clone DNA was subcloned into pGEM-7Z, and subjected to further restriction enzyme analysis.

Nucleotide Sequencing.

Suitably sized DNA fragments were subcloned into pGEM-7Z again as illustrated in FIG. 3A. Sequencing was performed with a sequencing kit (GIBCO-BRL) based on the dideoxy-chain termination method modified for use with double-stranded templates and Taq polymerase (Craxton (1991)). The sequences were analyzed by using TFSEARCH computer software. Oligonucleotide primers were synthesized according to either vector-specific sequences (T7 and SP6) or specific sequence of the exon 1 and exon 2 of the rat galanin gene (upper and lower primers) as described above. The sequencing strategy is showed in FIG. 3.

Primer Extension Analysis.

Total RBA from rat pituitaries was isolated by the guanidinium thiocyanate method (Chirgwin et al., (1979)). Poly (A) RNA was purified using poly A tract mRNA isolated System III (Promega) and was hybridized with the end-labelled oligoneucleotide primer (5'-AGGGTCGTCACTGCATGGC-3' SEQ. ID. NO. 7) which complementary to the regions +67 to +48 relative to the transcription stat site. Hybridization was carried out in 0.4 M naCl, 10 mM Pipes pH6.5 for two minutes at 85° C. and then five hours at 63° C. For the extension reaction, 0.5 mM DNTP and 1×RT buffer (Promega), 20 units RNase Inhibitor (Promega), 1.5 μg BSA and 400 units of M-MLV reverse transcriptase (Promega) were added and the incubation was at 42° C. for one hour. After extension, phenol/chloroform and ethanol preciptation the DNA/RNA hybrids were loaded on 6% polyacrylamide urea gel. The size of the primer extension products were determined by comparing with a sequencing ladder using the same primer for primer extension and the template plasmid containing the 5' Flanking region of the gene.

Cell Culture.

Human neuroblastoma cell line (SK—N—MC) was from Dr. A. Nath (Dept. of Medical Microbiology, U. of Manitoba), Hela cell line was from Dr. M. L. Duckworth (Dept. of Physiology, U. of Manitoba), Rat pheochromocytoma ($PC_{12}$) and rat pituitary $GH_3$ cell lines were purchased from the American Tissue Culture Collection (Rockville, Md.).

SK—N—MC cells were cultured in Dulbecco's modification of Eagle's medium (DMEM) with 2 mM L-glutamine, supplemented with 10% fetal calf serum (FCS), 1×Antibiotic-Antimycotic (GIBCO-BRL). Hela cells were cultured in DMEM medium plus 8% FCS and 1×Antibiotic-Antimycotic (GIBCO-BRL). $PC_{12}$ cells were cultured in DMEM medium and supplemented with 7% FCS, 7% horse serum and 1×Antibiotic-Antimycotic (GIBCO-BRL). $GH_3$ cells were cultured in DMEM medium with 10% FCS and Bonus. All of them were incubated at 37° C. in 95% air and 5% $CO_2$.

Construction of Luciferase Reported Plasmid.

A series of deletion mutants of rGAL 5' Flanking region of the galanin gene, which end within the first exon, were prepared by digestion of the 8 kb-Hind III PGEM-7Z clone with suitable combinations of restriction enzymes. The inserts were constructed into PXP2, a promoterless luciferase reporter gene vector (Nordeen (1988)).

The Glu-657 was obtained by digestion of the 8 kb insert with Kpn I. To create the Glu-486, the plasmid pGEM-657 containing the insert of the Glu-657 was digested with Kpn I and Pvu II, following by fill-in reaction with Klenow fragment, religated to pGEM-7Z and then subcloned into $pXP_2$. To prepare the Glu-208 and Glu-126, the pGEM-657 were cut with Kpn I/Rsa I and Kpn I/Ban II, respectively, following the same way of creating the Glu-486 construct described above.

Since convenient restriction sites for subcloning of the rat galanin promoter were not present in $pXP_2$, a 6 kb Hind III/Sac I fragment containing sequences approximately from −4500 to +1600 was subcloned into the $pXP_2$ vector forming the Glu-4500/1600. The Glu-4500/1600 was cut with Kpn I to remove the Kpn I-Sac I fragment and subcloned into pGEM-7Z. The $pXP_2$-Hind III/Kpn I plasmid containing the sequences from −4500 to −657. The $pXP_2$-Hind III/Kpn I was cut with Kpn I and ligated to a Kpn I fragment (−657 to +152) prepared form the Glu-657 in the sense orientation, generating the Glu-4500. All of the constructs were sequenced to assure the accuracy of the ligation.

Analysis of Transient Expression.

One or two days prior to transfection, cells were plated at a density about 2×10⁵ cells/60 mm dish. Briefly, cells were transfected with 6 μg of rGAL-luc construct and 1 μg of β-galactosidase expression vector (pCMV) using calcium phosphate transfection method (44); Cells were washed with phosphate-buffered saline (PBS) seven hours after transfection and treated with/without different drugs (such as TPA, estrogen, NGF) for 24–36 hours.

To assay the level of expression, the cells were lysed in 1×lysis buffer (Promega). 10 μl of luciferase substrate solution (Promega), and luciferase activity was measured by Beckman LS 600 Scintillation Systems, β-galactosidase activity was measured with a chemiluminescent reporter assay systems, Galacto-Light (Tropix). Within each experiment, luciferase activity was determined in duplicates or triplicates and normalized to β-galactosidase activity for each dish.

Nuclear Extract and Electrophoretic Mobility-shift Assays.

Nuclear extracts were prepared from cells of Hela, SK—N—MC, and SK—N—MC treated with $10^{-7}$ M TPA for 36 hours before harvest as according to published protocols (Dignam, et al., (1983)). The extracts were dialysed against 20 mM Hepes, pH 7.9, 20% (v/v) glycerol, 0.1 MKCl, 0.2 mM EDTA, 0.5 mM dithiothreitol (DTT) and 1 mM phenylmethylsulphony fluoride (PMSF) the nuclear extracts were aliquoted and stored at −80° C.

The binding reactions containing 1 μg poly (dI-dC), 6 μg of nuclear extract, 10 mM Hepes, pH 7.9, 10% (v/v) glycerol, 0.1M KCl, 0.2 mM EDTA, 0.5 mM DTT. Reaction were incubated for 15 minutes at room temperature with or without competitor DNA, the incubations were continued for additional 20 minutes after labelled probe were added. Competition was done using 10-, 40-fold molar excess of unlabelled probe. Samples were electrophoresed on 6ˆ non-denaturation polyacrylamide gels at 4° C. in 0.5×TBE buffer.

Results

Isolation and Cloning of the Rat Galanin Gene.

A rat liver genomic DNA library was amplified and screened using a PCR method as described in Material and Method. At each stage of screening (primary-secondary) the number of initial phage particles per tube was decreased (ex. 4×10⁴ pfu/tube to 1.6×10³ pfu/tube). In the primary screening 25 tubes were inoculated with 40,000 phage/tube, amplified and polled in 5×5 matrix as it is illustrated in FIG. 1. Pools from columns and rows were screened by PCR. For amplification of a 0.4 kb fragment of the rat galanin gene spanning exons 1–2, primers Gal 1 and Gal 2 were chosen. In the primary screening pools from rows a and b and polls from column E gave a 0.4 kb PCR product, which was subsequently positive as well by Southern hybridization to an oligonucleotide located between the Gal 1 and Gal 2 primers (FIGS. 2 A & B). Secondary and tertiary screening resulted in the isolation of three positive clones. Mapping of one 25 kb positive clone by Southern analysis and hybridization with the full length cDNA showed two Hind III fragments (an 8 kb and a 3 kb) to hybridize positively. Hybridization with the Gal 1 primer indicated that only the eight kb fragment contains more 51 end sequences. Further restriction analysis of the 8 kb fragment showed that it contains a 4.5 kb 5' Flanking region of the rat galanin gene as well as intronic sequences including intron 4. The second three kb Hind III fragment contains the two other exons and introns (5 and 6).

The 8 kb-Hind III fragment was subcloned to pGEM-7Z plasmid and was further characterized by restriction enzyme analysis as it is illustrated in FIG. 3. Two BamHI fragments (FIG. 3) including exon 1 and 2 and containing 1 kb of the 5' Flanking region were further subcloned and sequenced.

The structure of the 8 kb fragment is shown in FIG. 3. Sequencing of an 1.5 kb fragment as indicated in FIG. 3B revealed the presence of a TATA box-like element (TATAAATA) and that exon 1 consists entirely of noncoding sequences (+1 to +152) which is separated from exon 2 by 200 bp. Exon 2 (+352 to +432) begins with the site of translation initiation and codes for the first 27 aminoacides containing the signal peptide of the galanin precursor. The exon 1 and 2 sequence is in agreement with the rat cDNA sequence.

Figure 4:
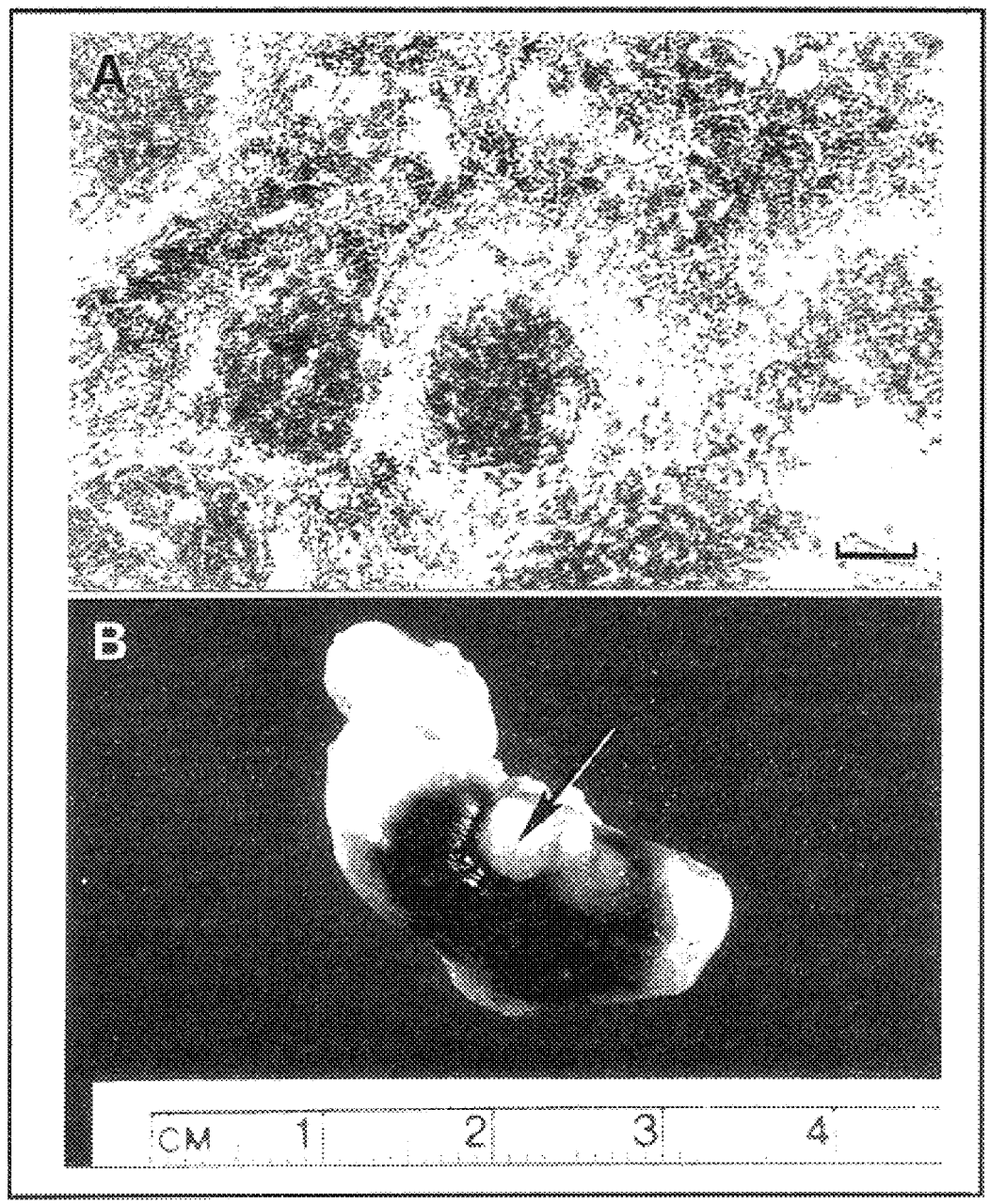
FIGS. 4A and 4B show an enlarged Lymphnode of the stomach (B) and Hemoloxylin-Eosin staining of paraffin section. Bar=1 μm=10 μm.

The DNA sequence of the rat galanin gene clone was searched using the TFSEARCH version 1.3 software for possible transcription factors consensus DNA binding sites. The results of the analysis along with the sequence are shown in FIG. 4. The following potential elements were found in the proximal promoter region: a TATA box-like element and some putative cis-elements including a perfect CREB, three half-palindrome EREs, several AP-1, AP-4, SP1, GATA etc (FIG. 4).

Determination of the Transcriptional Start Site.

The transcription start site of the rat galanin gene was mapped by primer extension (FIG. 2) using mRNA isolated from rat pituitaries. A 20-base oligonucleotide based in sequence in the exon 1 region of the rGAL cDNA and complementary to the sequence from +48 to +60 of the genomic clone, yielded a extension product of 68 bp in length (FIG. 2). The transcription start site is located in a G nucleotide of a TATA like box.

Basal Rat Galanin Promoter Activity in Neuronal and Endocrine Cell Lines.

To determine the role of transcriptional elements in the functional activity of the galanin promoter and to locate potential tissue-specific positive and negative control elements, a series of deletions of the promoter region were constructed. Fragments containing various lengths of the 5' Flanking sequence of the rat galanin gene including the entire first exon were fused with the promoterless $pXP_2$ vector containing the coding sequence of the luciferase gene as indicated in FIG. 3C. To obtain the Glu-4500, Glu-657, Glu-486, Glu-208 and Glu-126, respectively constructs.

Figure 5A:
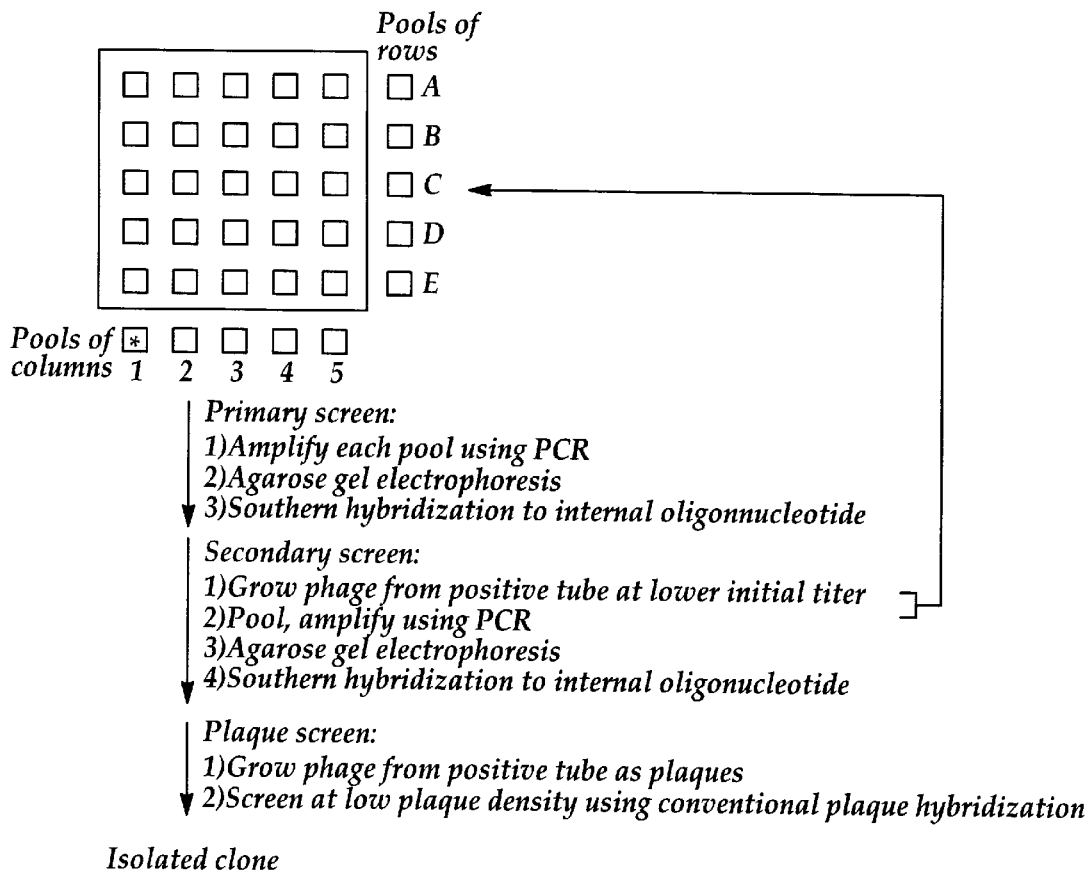
FIGS. 5A and 5B show a diagram of PCR screening; Panel A: Schematic diagram of the PCR screening procedure (modified from Isral, D. I. 1993); Panel B: Diagrammatic representation of the PCR product detectable by hybridization; the locations of the PCR primers and the hybridization oligonucleotide between exon 1 and exon 2 of the rat galanin gene are shown, with the correct PCR product of 383 bp hybridizes to the internal hybridization oligonucleotide.

Each construct was transfected to neuronal, non-neuronal and endocrine cell lines (SK—N—MC, $PC_{12}$, $GH_3$ and Hela) and basal levels of Luc-activity were determined. After correction for transfection efficiency by the CMV-galactosidase activity, the activity of the different constructs in the above mentioned cell lines were calculated as fold increase above the $pXP_2$ basic activity. Every measurement was in triplicates and repeated at least in three independent experiments. The results of the luciferase assay showed that galanin promoter was actively transcribed in $GH_3$ $PC_{12}$ and SKN—N—MC cell line (FIG. 5A).

Basal activity was increased for all three cell lines unless a 4 kb fragment was removed from the 5' end (construct Glu-4500 to Glu-486).

This data indicate that positive regulatory elements are located within at least the 200 bp of the 5' flanking region with the strongest activity within the 486 bp, while repressor elements are located upstream of the 486 bp region.

It is also indicated from these experiments that a strong neuronal tissue specific element is located up to 657 bp of the 5' flanking region that is not active in the endocrine cell line $GH_3$ No activity is detected in the Hela cell line with any of above constructs, while reverse orientation of the Glu-657 construct in $pXP_2$ plasmid abolished the activity completely.

It was also interesting that another construct (−657 to +1600) including the first two intronic sequence diminished the activity significantly indicating that a strong repressor element is also located within the first two intronic sequences.

Induction of Galanin Promoter Activity by TPA, NGF and Estrogen.

The previously mentioned rat galanin 5' flanking gene constructs were transfected in the same cell lines. After treatment for 24 to 36 hours with the above agents, the cells were harvested and their activity was measured.

Figure 5B:
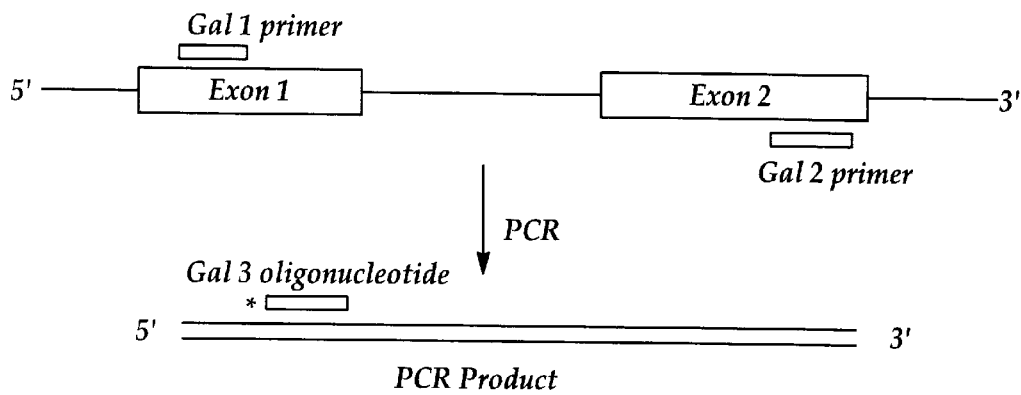
Figure 9A:
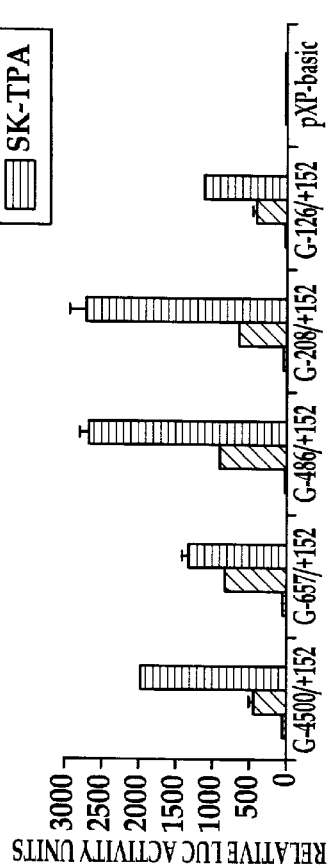
FIGS. 9A–9D show the rat galanin gene promoter activities; A shows fold increase of the rat galanin gene promoter activity in the Hela, SK—N—MC, $PC_{12}$ and $GH_3$ cell lines, these cells were transfected the plasmids containing the luciferase reporter gene under no promoter ($pXP_2$), the pCMV used as a transfection efficiency control; after transfection for 36 hours, cell extracts were assayed for luciferase and β-galactosidase activities, each value represents triplicate transfections from one representative experiment; B shows rat galanin gene promoter activity in the Hela and SK—N—MC cells (in arbitrary units), after transfection and treatment with TPA or vehicle for 36 hours, cell extracts were assayed for luciferase and β-galactosidase activities, each value represents duplicate transfections from one representative experiment; C shows fold increase of the rat galanin gene promoter activity in the SK—N—MC, $PC_{12}$ and $GH_3$ cells, the cells were transfected the plasmids containing the luciferase reporter gene under no promoter ($pXP_2$), description as in panel A and each value represents duplicate transfections from one representative experiment; D shows the fold increase of the rat galanin gene promoter activity in the $GH_3$ cell line, description as in panel A.
Figure 9B:
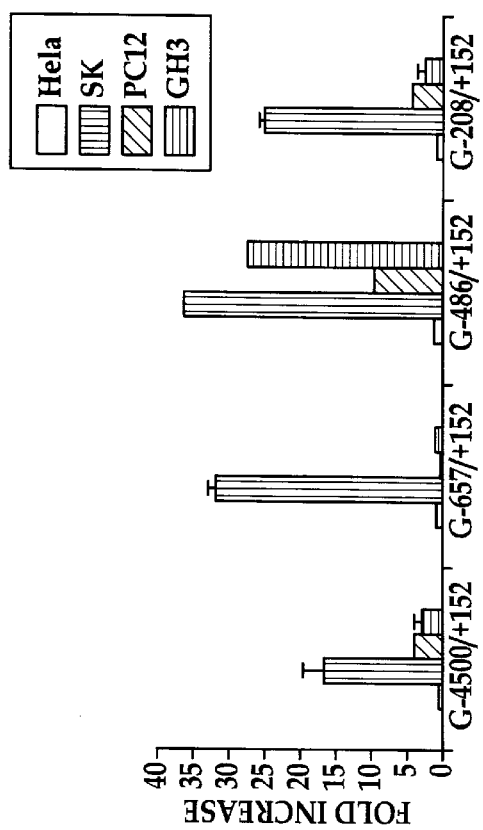
Figure 9C:
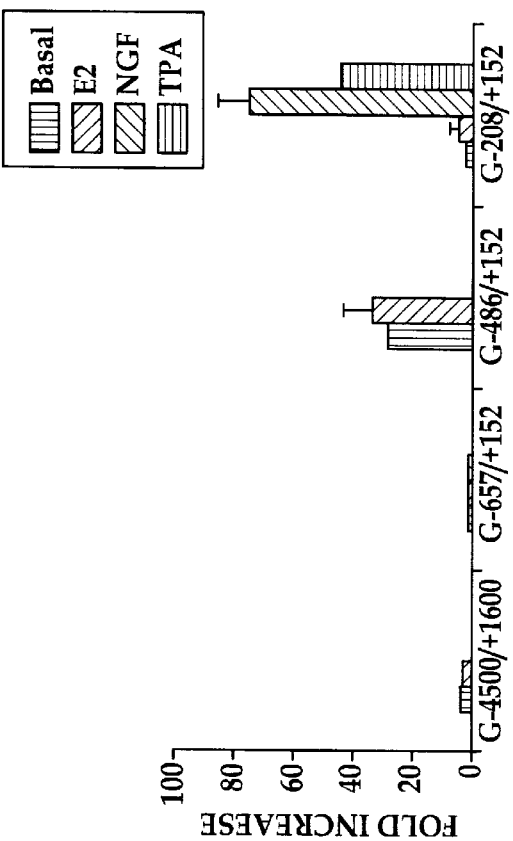
Figure 9D:
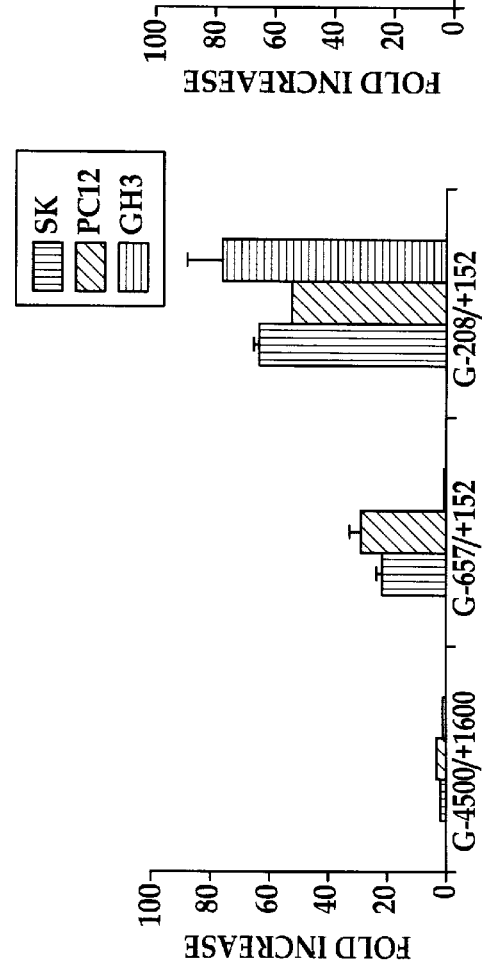
Figure 10A:
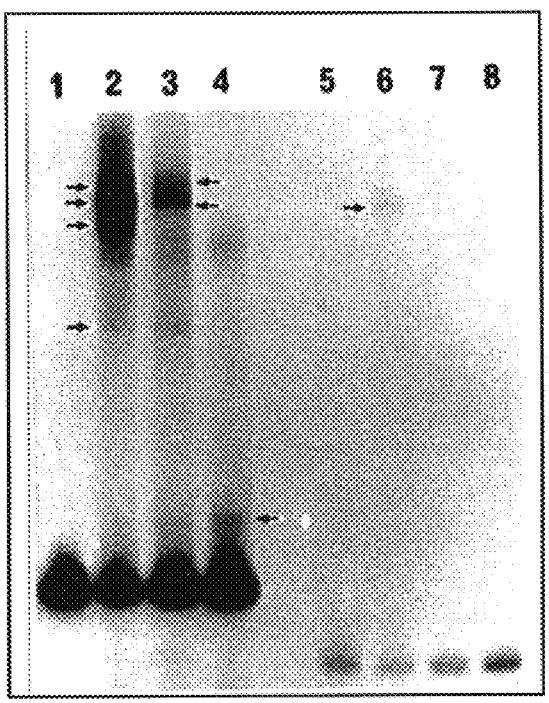
FIGS. 10A and 10B show a mobility gel shift; gel shift analysis of the oligonucleotide from the −208 to +13 region of the rat galanin gene, the positions of the protein-DNA complexes are denoted by arrows, and specific competition with increasing amounts (as fold molar excess) of the unlabelled homologous oligonucleotides (lane d to g) is shown; lane a shows the probe in the absence of the protein; lane b, the probe with the presence of the Hela nuclear extract; lane c, the probe with the presence of the SK—N—MC cell nuclear extract; lane d, the probe with tenfold molar excess of the unlabelled homologous oligonucleotide in the presence of the Hela nuclear extract; lane e, the probe with tenfold molar excess of the unlabelled homologous oligonucleotide in the presence of the SK—N—MC nuclear extract; lane f, the probe with 40-fold molar excess of the unlabelled homologous oligonucleotide in the presence of the Hela nuclear extract; lane g, the probe with 40-fold molar excess of the unlabelled homologous oligonucleotide in the presence of the SK—N—MC nuclear extract; Panel B shows a gel shift analysis of the oligonucleotides from the −208 to −126 (lane 5–8) and −126 to +13 (lane 1–4) regions of the rat galanin gene, gel shift assays were performed with either Helan or SK—N—MC or SK—N—MC treated with $10^{-7}M$ of TPA cell nuclear extract, the positions of the protein-DNA complexes are denoted by arrows; lane 1 shows the probe of −126/+13 in the absence of proteins; lane 2 shows the probe of −126/+13 in the presence of nuclear extract from Hela; lane 3, the probe of −126/+13 in the presence of nuclear extract from SK—N—MC; lane 4, the probe of −126/+13 in the presence of nuclear extract from SK—N—MC/TPA; lane 5, the probe of −208/−126 in the absence of proteins; lane 6, the probe of −208/−126 in the presence of nuclear extract from Hela; lane 7, the probe of −208/−126 in the presence of nuclear extract from SK—N—MC; lane 8, the probe of −126/+13 in the presence of nuclear extract from SK—N—MC/TPA.
Figure 10B:
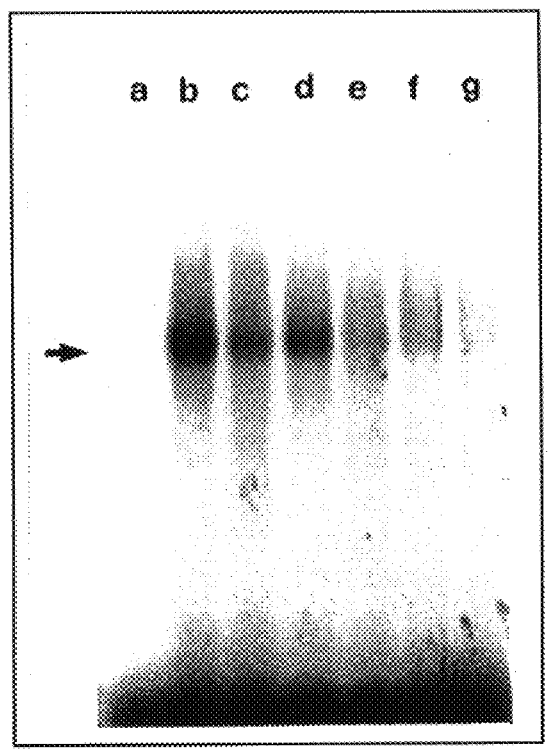

TPA strongly induced promoter activity of the galanin gene in the SK—N—MC cell line over and above the basal activity by 4–5 fold (FIG. 5B). High activity was sustained from the Glu-4500 construct through the Glu-126 construct indicating that a strong TPA responsive element is located within the first −126 bp of the galanin promoter with the highest response located in the 200 bp. Similarly in the $GH_3$ cell line, a strong TPA responsive element was located within the −200 bp of the promoter (FIG. 5D) while no significant response was noted in the $PC_{12}$ cells.

NGF also stimulated galanin promoter activity in both neuronal and endocrine cell lines (SK—N—MC, $PC_{12}$ and $GH_3$) with the highest stimulation in the $GH_3$ cell line. The strongest stimulation in all three cell lines were located within the first −126 bp of the galanin promoter with the highest response located in the 200 bp. Similarly in the $GH_3$ cell line, a strong TPA responsive element was located within the −200 bp of the promoter (FIG. 5D) while no significant response was noted in the $PC_{12}$ cells.

NGF also stimulated galanin promoter activity in both neuronal and endocrine cell lines (SK—N—MC, $PC_{12}$ and $GH_3$) with the highest stimulation in the $GH_3$ cell line. The strongest stimulation in all three cell lines were located within the 200 bp region of the promoter (FIG. 5C).

Estrogen had a very weak effect that was not significant in the SK—N—MC cells while in the $GH_3$ cells were significant in the Glu-208 and Glu-126 constructs (almost two fold over and above the basal stimulation) although not always consistent FIG. 5D).

Gel Mobility Shift Assays.

Since the highest activity of the galanin (both basal and drug induced) was demonstrated in the 200 bp of the 5' Flanking region, the ability of the fragment to bind putative transcription factors in nuclear extracts was examined. Gel mobility shift assay was used to examine the binding activity of the region to proteins present in nuclear extracts prepared from SK—N—MC (with or without TPA treated) and Hela cells as well.

When the −208 to +13 fragment was tested, a prominent retarded band was observed from both SK—N—M—NC and Hela cells. Competition experiments using 10-fold and 40-fold molar excess of the same unlabelled fragment decreased the intensity of this band proportionally indicating the specificity of this binding.

To further locate the cis-acting elements two other fragments were generated in this region, the −208 to −126 and the −126 to +13 fragments. Gel shift assay with the −208 to −126 fragment gave a strong retarded band in the Hela extracts with less prominent band in the SK—N—MC extract while treatment of SK—N—MC cells with TPA abolished this band. Gel shift assay with the −126 to +13 fragment generated among others a retarded band that was unique in the SK—N—M—NC extract and that was increased after TPA treatment.

Discussion

Galanin is a highly conserved neuropeptide, expressed in both neuronal and endocrine tissues and which is upregulated in a tissue specific manner. In order to examine the transcriptional activation of the galanin gene and to determine functionally active regulatory elements a genomic clone (25 kb) was isolated containing the whole rat preprogalanin gene including at least 4.5 kb of the 5' Flanking region.

Partial sequence analysis of the rat galanin gene revealed several interested features. The sequence of the proximal promoter is quite conserved among species examined so far (human, mouse, bovine) (Kofler, et al., (1996); Kofler, et al., (1995); Rokeus, et al., (1994); Anouar, et al., (1994)). The first exon in all four species (rat, mouse, human, bovine) encodes the 5' untranslated region while exon 2 start with the first codon of the translation initiation methionine. Therefore the regulation of the galanin gene are conserved as well among species The present transfection data indicated that the rat galanin gene is transcriptionally activated in both neuronal and endocrine cell lines, while no activity was detected in Hela cells. The highest basal activity was detected in SK—N—MC cells indicating that the basal promoter activity of the galanin gene is cell type specific. This explains the wide distribution of galanin in the central and peripheral nervous system.

The highest activity in all cell lines was observed in the Glu-486 construct (−486 to +152) while the Glu-4500 construct (−4500 to +152) had at least 2–3 fold ess activity indicating that both negative and positive regulatory elements exist in the rat galanin gene. This is consistent with reports for the human (Kofler, et al., (1995)) and bovine galanin gene (Rokeus, et al., (1994); Anouar, et al., (1994)) containing negative regulatory elements as well, and with some very preliminary reports for the proximal region of the rat galanin gene (Kaplan, et al. (1991)).

Experiments have also shown that in the rat galanin gene, the negative regulatory elements appeared to be tissue specific since they are located differently in the SK—N—MC and $GH_3$ cells (activity t Glu-657 versa Glu-486 in the two cell lines) with a stronger cell specific silencer element in the $GH_3$ cells while the minimum segment conferring neuroendocrine activity is the 126 bp of the galanin promoter. These differences could account for the differential expression and regulation of the galanin gene in neuronal and endocrine tissues. Furthermore, these negative regulatory elements could account for the transient expression of galanin during development. In both neuronal and endocrine tissues galanin is transiently increased during fetal and neonatal life (Xu, et al., (1996); Giorgi, et al., (1995)).

It has also been shown that the rat galanin promoter responded very strongly to TPA in both the SK—N—MC and the $GH_3$ cells. Although the response was sustained high from Flu-4500 to Glu-126 construct, the highest activity and highest fold increase (five fold) over the basal activity was noted in the Glu-208 construct.

It is possible that sequences on the first 200 b of the rat galanin promoter or on the first exon are responsible for the TPA induction of galanin activity in those cells. As it is indicated in FIG. 4 it is noted that consensus sequence for AP-1 and CREB binding are located in this region, which may be are induced by TPA.

The removal of the AP-1 element (pGlu-208 to pGlu-126) diminished the TPA response by two fold indicating that cooperation of both elements increases the TPA response. TPA response has also been found in the promoter of the bovine galanin gene (Anouar, et al., (1994)) indicating that the response to TPA is conserved among species. It is shown that the bovine galanin promoter contains a GTRE (galanin TPA responsive element) motif in the proximal promoter (TGACG), that has the consensus sequence for CREB (cAMP responsive element) binding site. The present rat genomic sequence has as well that TGACG (CREB ½ site motif in the same region indicating that the GTRE responsive element is identical in these two species. Mutation analysis of this motif confirms the functional activity of this GTRE in the rat galanin promoter as well.

NGF (nerve growth factor) stimulated rat galanin promoter activity significantly in both neuronal and endocrine cell lines. The highest response was noted in the Glu-208 construct indicating again that strong negative NGF responsive elements are located upstream of the 200 bp 5' Flanking region. Differential regulation of the negative and positive NGF responsive elements of the galanin promoter could account for the either positive or negative effect of NGF on galanin mRNA depending on the tissue and the environmental conditions. For instance, while NGF induces galanin gene expression in the rat basal forebrain (Planas, et al., (1997)), it has no effect on galanin expression in DRG (dorsal root ganglia) cell culture or in vivo after axotomy (Kerekes, et al., (1997); Zhang, et al., (1996)).

There is a 12 fold increase over and above the basal stimulation in the Glu-208 construct that it is even higher than the response in $PC_{12}$ cells, which are traditionally considered the most responsive cell line to NGF. Previously, it has been reported that NGF increases the differentiation of the $GH_3$ cells into the manotroph phenotype with increased secretion of PRL, while both the gp140trk and the gp75 NGF receptors are expressed in these cells (Missale, et al., (1994); Missale, et al., (1995)). On the other hand, transgenic mice overexpressing NGF in their lactotroph cells have exhibited dramatic hyperplasia (Borrelli, et al., (1992)). NGF and its receptor are constitutively expressed in mammal pituitary (Patterson, et al., (1994)).

Since NGF stimulates the transcription of galanin in the $GH_3$ cells, and since it has been shown that galanin transgenic mice overexpressing galanin in their pituitary, develop pituitary tumors, it can be hypothesized that NGF possibly affects pituitary hyperplasia through activation of the galanin gene. Further experiments will confirm the hypothesis.

Finally, in $GH_3$ cells there was a two fold increase over the basal level for the Glu-208 and Glu-126 constructs, not always consistent. Despite the dramatic upregulation of galanin mRNA by estrogen (12) and the three EREs ½ in the estrogen response experiments (PRL promoter) without contransfection of the estrogen receptor (Day, et al., (1990); Nowaakowski, et al., (1994)) indicating that the cells are normally responsive to estrogen. It is are possible that some other element is required to co-operate with the estrogen receptor to confer the estrogen response.

Since the Glu-208 construct had the highest activity (both basal and TPA, NGF induced), this sequence (oligo −208 to +13) was used in a gel mobility shift assay with nuclear extracts prepared from SK—N—MC and Hela cells. A prominent retarded band was observed in both extracts. This binding activity was repeatedly increased in the Hela nuclear extracts compared to equivalent amount of SK—N—MC nuclear extracts, while competition experiment with 10 to 40 fold molar excess of the same unlabelled fragment decreased the intensity of the shift band proportionally. Since galanin promoter is inactive in Hela cells and yet the intensity of the shift band is more prominent, this binding protein is possibly a repressor protein that negatively regulates galanin promoter activity. Furthermore, mobility shift assay with a −208 to −126 and −126 to +13 oligonucleotide further revealed that besides the negative regulatory element, another positive regulatory element is located in the −126 to +13 region which binding activity increased in SK—N—MC cells compared to Hela cells and its density is further increased by TPA treatment indicating that correspond to a positively regulated transcription factor.

The observations suggest that negative regulation is also utilized by neuronal cells to restrict expression of certain genes to subpopulation of neurons. Identification of similar inhibitory factors or negative regulatory elements which seem to repress gene expression has been described before for rPRL and GH genes (Nachtigal, et al., (1992); Jackson, et al., (1992)) and for the type II sodium channel gene (Kraner, et al., (1992)).

In summary, stimulation of the galanin gene transcription in neuro-endocrine cells are mediated by both an negative and positive regulatory elements. Identification of such elements that confer neuronal specific and TPA response have been located within the first 200 bp of the galanin promoter. Characterization of these binding proteins might provide means of identifying the exact involvement of galanin in conditions such as nerve regeneration or Alzheimer's disease.

Example 7

Axonal Regeneration in Galanin Transgenic Mice

As previously stated, galanin is a neuropeptide that is significantly elevated after nerve injury indicating that it might participate in nerve regeneration. This is tested by using a morphological and functional test, that the recovery of sciatic nerve crush in galanin transgenic mice is faster and more complete than the non transgenic litter mates. Thus, the use of the galanin transgenic model, where galanin is over expressed and over secreted, will define if galanin facilitates the recovery and regeneration of injured neurons and the potential therapeutic use of galanin in nerve regeneration and neuropathic pain.

Axonal injury provides a very useful paradigm to study cellular response to injury, mechanisms of regeneration and processes that lead to nerve cell degenerations. Moreover models of axotomy are valuable for testing experimental therapeutic approaches.

Background

Autonomic, sensory and motor neurons are capable of regenerating in adult mammals following axonal damage. (Jessel, (1991); Hendry, (1992)) Large changes in gene expression occur in the cell bodies of the axotomized neurons including decrease in the expression of proteins used for synaptic transmission and increase of expression of a number of proteins involved in regeneration (Zigmond, (1997); Ma, et al., (1997)). One characteristic of axotomized neurons is that they increase expression of galanin and VIP, indicating that these peptides may play. important role in the survival and regeneration of injured neurons (zhang, et al:, (1993); Hoekfelt; et al., (1994); Villar, et al., (1989)).

Nerve injury increases galanin levels dramatically in sensory neurons (Hoekfelt, et al., (1987); Kashiba, et al., (1992); Vilar, et al., (1991)) trigeminal sensory neurons (Unemoto, et al., (1994); Arvidsson, et al., (1994)), as well as in cranial mononeurons (Herdegen, et al., (1993); Moore, et al., (1989); Rutharfurd, et al., (1992); Saika, et al., (1991)) and adrenal ganglia cells (Dagerlind, et al., (1995)). A similar effect of axotomy has been described in sympathetic ganglia (Mohney, et al., (1994); Rao, et al., (1993); Schreiber, et al., (1994)). These findings suggest that galanin participates in cellular events characteristic for injured neurons.

Galanin exerts an analgesic effect after intrathecal administration to mice in both the tail flick and hot plate test (Post, et al., (1988)) and potentiates the spinal analgesic effect of morphine in the hot plate (Wiesenfield-Halin, et al., (1990)). Moreover application of high affinity galanin receptor antagonists enhances the noniceptive reflex induced by conditioning stimulation, and this effect is much higher in axotomized than in normal rats, suggesting increased release of galanin following axotomy and that the role of galanin in depression of spinal excitability is enhanced upon nerve injury (Wiesenfeld-Halin, et al., (1992)). Furthermore chronic administration of the galanin antagonist, M35 for 10 days after nerve transection caused a significant increase in self-mutilation (autotomy) (Verge, et al., (1993)). Similarly galanin antisense oligonucleotide induces autotomy in rats after axotomy (Ji, et al., (1994)). This suggests that the neuropathic pain arising from the peripheral injury is under the inhibitory control of endogenous galanin.

Very recently, several groups have almost simultaneously cloned and characterized two types of galanin receptors GalR1 and GalR2 (Wang, et al., (1997); Parker, et al., (1995); Burgerin, et al., (1995); Howard, et al., (1997); Sullivan, et al., (1997); Habert-Ortoli, et al., (1994)). The GalR1 receptor is abundant in the brain, the spinal cord, spinal ganglia and primary sensory neurons (Sullivan, et al., (1997); Habert-Ortoli, et al., (1994); Gustafson, et al., (1996); Xu, et al., (1996)). galanin receptor (GalR1) gene is tightly linked to the myelin protein gene on chromosome 18 in mouse (Simoneaux, et al., (1997)). Developmentally both galanin and galanin receptor(GalR1) are already expressed in trigeminal and dorsal root ganglion neurons by day 14(E14) (Xu, et al., (1996)).

In an attempt to further define the role played by galanin in the nervous and endocrine system, transgenic mice were generated over expressing and over secreting galanin. Galanin serum levels are ten times higher in the transgenic mice as compared to non transgenic litter mates (submitted). Since galanin levels are much higher in the transgenic mice as compared to non transgenic animals, regeneration processes of axotomised neurons will be much improved.

Methods and Experimental Design

Male galanin transgenic and non transgenic animals of same weight and similar age were used. Under anaesthesia (avertin), the right sciatic nerve was exposed and crushed firmly with a fine watchmaker's forceps for two 15-seconds periods at mid thigh level, using the same force at 90 degrees angle. A single 8–0 black silk epineurial suture was placed as a marker for identification purposes. The muscles and skin was closed in layers. As controls, both transgenic and non transgenic animals were anaesthetized and the sciatic nerve were exposed without being crushed.

Animals were allowed to survive for different time points (6, 14, 21 days) after crush. For each group, 20 animals were used. The same animals were used for the functional tests as well.

Morphological Studies

At the end of the point periods, animals were perfused va the ascending aorta with a mixture of 4% paraformaldehyde, 0.5% glutaraldehyde in 0.1M Phosphate buffer. After perfusion, the L4–L5 lumbar spinal segment the L4–L5 dorsal root ganglia and the proximal and distal of the crush, axons of the sciatic nerve were removed (the proximal and distal side of each segment will be labelled for further identification). Both ipsilateral and contralateral tissues were removed and postfixed in 1% OsO4 for three hours. After ethanol dehydration and epoxy resin infiltration, each nerve was divided into a proximodistal series of blocks which were equal in length. Each block was then embedded so that its proximal end was sectioned transversely.

Microscopic observation and morphometry were performed in semithin sections (1 μm) stained with toluidine blue. Electron microscopy was performed on uranyl acetate and lead citrate stained thin sections. Serial sections of 0, 2, 4, 6, 8, and 10 mm distal to the site of lesion were taken and stained with toluidene blue.

All morphometric studies were performed with the aid of a Sigma Scan Complete Measurement System (Jandel Scientific) using a personalized computer and a digitizing table. The external cross-sectioned area and the axonal area of the nerve fibers were determined. The g-ratio area, i.e. axonal area/external area, were also calculated and used as an index of demyelination or axonal atrophy. Both light and electron microscopy was used to obtain endoneurial areas and total numbers of myelinated and unmyelinated axons. Axon-melin ratios were calculated from 30 randomly chosen myelinated fibers from each animal at the 10 mm distal segment. Electron micrographs at 62,700× were used for these calculations. The natural logarithm of the axonal area was digitized and plotted against the number of myelin lamellae of the corresponding myelin sheath.

Photomicrographs of two sections (separated by five other sections) from the middle of the L4 dorsal and ventral root ganglia were used to determine cross-sectioned areas. Ipsilateral and contralateral sensory and motor neurons were counted blindly on every fifth section throughout the ganglia.

Figure 11A:
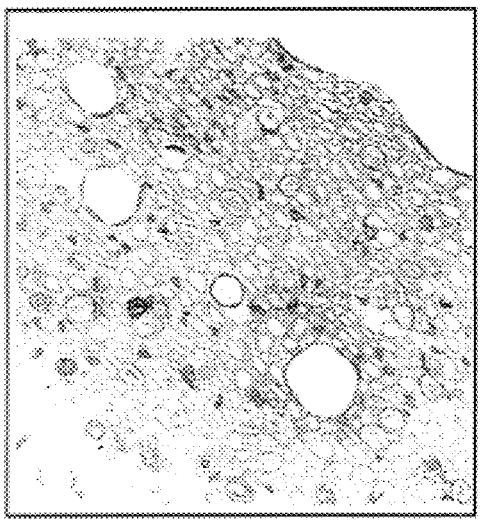
FIGS. 11A–11C show the light microscope photomicrographs of sciatic nerve toluidine blue-stained transverse section (Distal segment 10 mm), 15 days after crush; A=non transgenic animal, B=transgenic animal, C=control animal.
Figure 11B:
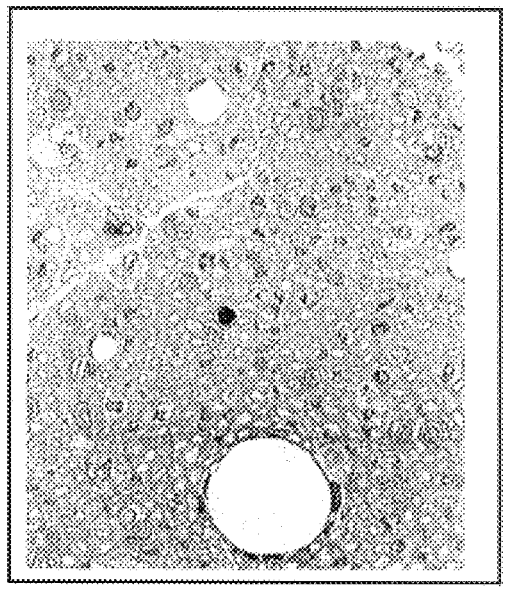
Figure 11C:
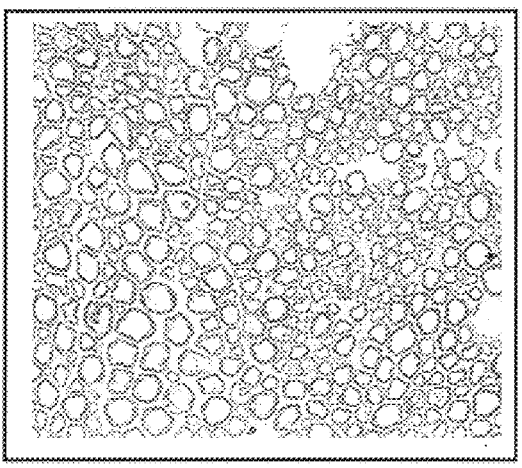

Results (FIG. 11) indicate that the distal segment of the sciatic nerve in the transgenic animals is less damaged (or faster regenerated) than the non transgenic.

Immunohistochemistry.

Three animals from each group were processed for immunihistochemistry studies. Briefly, animals were perfused intracardially, first with phosphate-buffered sale (PBS) and then with 10% buffered formalin. The same as previously mentioned tissues were removed, post fix for six hours and paraffin embedded. Sections of 10 μm were incubated with a rabbit polyclonal anti-rat (rat galanin is 99% identical to mouse galanin) galanin antibody in 1:3000 dilution for 48 hours at four degrees. Subsequently, the sections were processed using the biotin peroxidase antiperoxidase system.

Statistical Analysis.

Comparisons between the different time point periods of transgenic non transgenic and control animals were performed using the two-way ANOVA test. Similarly, comparison of the morphometric data of the distal axon at 0 to 10 mm distance were performed within the same animal and between animals.

Functional Tests.

Prior to surgery and every three days after surgery, transgenic, non transgenic and control animals were subjected to the following tests:

Recovery of Reflex Motor Function.

The recovery of the reflex motor function was tested by the vestibular placing response, spreading of the toes, after sudden lowering the animal toward the ground ( ). The first sign of recovery was the abduction of the first digit in the following days Degree of digital fanning were measured by inking the toe pad.

Swimming.

Mice were trained to swim prior to the operation on a one and half meter long and 20 cm wide glass tank custom made. The timing (speed) of each individual mice were recorded and each mice will be videotaped for further kinematically analysis. On each session, the joint angle excursion was measured on each frame along with the number of full movements per minute.

Hot Plate Test.

The latency of paw withdraw following the application of heat was measured for both the operated and the control hid paw. The apparatus is consisting of a glass bottomed chamber under which is a focused light source aimed to at the planter surface of the hind paw which is used as the heat source. When the light is turned on; it automatically starts a timer. Photo sensors around the light source detect the removal of the paw and the light source automatically turns off and the timer will stop. The maximum stimulus was 15 seconds to avoid blistering of the foot pad.

Discussion.

Axonal injury provides a very useful paradigm to study cellular response to injury, mechanisms of regeneration and processes that lead to nerve cell degenerations. Moreover, models of axotomy are valuable for testing experimental therapeutic approaches. The present galanin transgenic model enhances the understanding and potential therapeutic use of galanin in nerve regeneration and neuropathic pain.

Throughout this application, various publications, including United States patents, are referenced by author and year and patents by number. Full citations for the publications are included. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

References

Merchenthaler I, Lopez F J, Negro-Vilar A, Anatomy and Physiology of central galanin containing pathways. Progr. Neurobiol. 40, 711–769 (1993).

Vrontakis M E, Torsello A, Friesen H G, Galanin—A review. J. Endocrinol. Inv. 14, 785–794 (1991).

Ottlez A, Snyder G D, McCann S M, Regulatory role of galanin in control of hypothalmic-anterior pituitary function. Proc. Natl. Acad. Sci. USA 85, 9861–9865 (1988).

Gabriel S M, Milbury C M, Nathensan J A, Martin J B, Galanin stimulates rat pituitary growth hormone secretion in vitro. Life Sci. 42, 1981–1986 (1988).

Wynick D., Hammond P J, Akinsanya K O, Bloom S R, Galanin regulates basal and cestrogen stimulated lactotroph function. Nature 364, 529–532 (1993).

Murakami Y et al., Possible mechanisms involved in growth hormone secretion induced by galanin in the rat. Endocrinology 124, 1224–1229 (1989).

Koshiyama H. et al., Central galanin stimulates pituitary prolactin secretion in rats. Neurosci. Lett. 75, 49–54 (1987).

Vrontakis M E et al., Estrogen induction of galanin synthesis in the rat anterior pituitary gland demonstrated by in situ hybridization and immunohistochemistry. Neurosci. Lett. 100, 59–64 (1989).

Kaplan L M et al., Galanin is an estrogen inducible secretory product of the rat anterior pituitary. Proc. Natl. Acad. Sci. USA 85, 7408–7412 (1988).

Steed J et al., Galanin and vasoactive intestinal peptide are colocalized with classical pituitary hormones and show plasticity of expression. Histochemistry 93, 183–189 (1989).

Hyde J F, Engle M G, Maley B E, Colocalization of galanin and prolactin within secretory granules of anterior pituitary cells in estrogen treated Fischer 344 rat. Endocrinology, 129, 270–276.

Vrontakis M E et al, Isolation and characterization of a complementary DNA (galanin) clone from estrogen induced pituitary tumor. J. Biol. Chemi. 262, 16755–16788 (1987).

Moore J. Morrison D, Hyde J F, Galanin gene expression is increased in the anterior pituitary gland of the human growth hormone-releasing hormone transgenic mouse. Endocrinology 134, 2005–2010 (1994).

Leile V, Vrontakis M, Kasper S, Friesen H, Bromocriptine inhibits galanin gene expression in the rat pituitary gland. Molec. Cel. Neurosci. 4, 418–423 (1993).

Rutherford S D, Widdop R E, Lauis W J, Gundlech A L, Preprogalanin mRNA is increased in vagal motor neurons following axotomy. Mol. Brain Res. 14, 261–266 (1992).

Mohney R P, Siegal R E, Zigmonl R E, Galanin and vasoactive intestinal peptide messenger RNA as increase following axotomy of adult sympathetic neurons. J. Neurobiol. 25, 108–118 (1994).

Karin M et al., Tissue specific expression of the growth hormone factor-1. Rec. Prog. Horm. Res. 46, 43–58 (1990).

Borreli E et al., Transgenic mice with inducible dwarfism. Nature 339, 538–541 (1989).

Behringer R R, Mathems L S, Palmiter R D, Brinster R L. Dwarf mice produced by genetic ablation of growth hormone expressing cells. Gen. Devel. 2, 453–461 (1988).

Howard A D, et al., Molecular cloning and characterization of a new receptor for galanin. FEBS Lett. 405, 285–290 (1997).

Sallivon K A, Shiao L L, Casievi M A, Pharmacological characterization and tissue distribution of the human and rat Gal R1 receptor. Bioch. Biophys. Res. Commun. 233, 823–828 (1997).

Evans H. Bammgartner M, Shine J, Herzog H., Genomic organization and localization of the gene encoding human preprogalanin. Genomics 18, 473–477 (1993). Dr. Brontakis.

Sethi T, Rezengurt E, Multiple neuropeptide stimulate clonal growth of small cell lung cancer; effects of bradykinin vasopressin, cholecyst kinin, galanin and neuroleusin. Cancer Res. 51, 1674–1679 (1991).

Ji R R, et al., Central and peripheral expression of galanin in response to inflammation. Neurosci. 68, 563–576 (1995).

Palkovits M, Neuropeptide messenger plasticity in the CNS following axotomy. Mol. Neuorobiol. 10, 91–103 (1995).

Vrontakis M E, Schroedtr I, Cosby H, Friesen G H, Expression and secretion of galanin, during pregnancy in the rat. Endocrinology 130, 458–464 (1992).

Lopez J and Talamantes F, Secretion kinetics of prolactin and growth hormone by mouse anterior pituitaries in long term organ culture. Life Sci. 32, 2103–2106 (1983).

Merchenthaler, I., Lopez, F.-J, & Negro-Vilar, A. (1993) Progress in Neurobiol. 40, 717–769.

Bartfai, T., Hoekfelt, T., & Langel, U. (1992) Curr. Rev Neurobiolog. 7, 229–274.

Rokaeus, A. (1987) TINS 10, 158–164

Vrontakis, M.-E., Torsello, A., & Friesen, H. G. (1991) J. Endocr. Inves. 14, 785–794

Melander, T., Straines, W.-A., Hoekfelt, T., Rokaeus, A., Eckenstein, F., Salraterra, P., & Wainer, B. (1985) Brain Res. 360, 130–138

Skofitsch, G., & Jacobowitz D.-M. (1986) Peptides 7, 609–613

Bedecs, K., Berthold, M., & Bartfai, T. (1995) J. Biol. 27, 337–349

Gentleman, S.-M., Falkai, P., Bogerts, B., Herrco, M.-T., Polak, J.-M., & Poberts, G.-W. (1989) Brain Res. 505, 311–315

Vrontakis, M.-E., Peden, L.-M., Duckworth, M.-L., & Friesen, H.-G. (1987) J. Biol. Chem. 262, 16755–16759

Kaplan, L.-M., Spindel, e.-R., Isselbacher, K.-J., & Chin, W.-W. (1988) Proc. Natl. Acad. Sci. USA 85, 1065–1069

Vrontakis, M.-E., Sano, T., Kovacs, K., & Friesen, H.-G (1990) J. Chin. Endocrinol. Metabo. 70, 747–751

Vrontakis, M.-E., Yamamoto, T., Schroeder, L.-C., Nagy, J.-I., & Friesen, H.-G. (1989) Neurosci. Lett. 100, 59–64

Bauer, f., Adrian, T.-E., Christofides, N.-D., Ferri, G.-L., Yanaihara, N., Polak, J.-M., & Bloom, S.-R (1986) Gastroenterology 91, 877–883

Wiesenfeld-Hallin, Z., Bartfai, T., & Hoekfelt, T. (1992) Front. Neuroendocrinol. 13, 319–343

Dunning, B.-E., Ahren, B., Veith, R.-C., Bottcher, G., Sunoller, F., & Taborsky, G. (1986) Amer. J. Physiol. 251, E127–133

Evans, H.-F., & Shine, J. (1991) Endrocinol. 129, 1682–1684

Rokaeus, A., & Brownstein, J.-J. (1986) Proc. Natl. Acad. Sci. USA 83, 6287–629

Rokaeus, A., & Carlguist, M. (1988) FEBS Lett. 234, 400–406

Lundkvist, J., Land, T., Kahl, K., Becedes, K., & Bartfai, T. (1995) Neurosci. Lett. 200, 121–124

Norberg, A., Sillard, R., Carlquist, M., Jornvall, H., & Mutt, V. (1991) FEBS Lett. 288 151–153

Tatemoto, K., Rokaeus, A., Jornvall, H., McDonald T.-J., & Mutt, V. (1983) FEBS Lett. 164, 124–128

Sillard, R., Langel, U., & Jornvall, H. (1990) Pept. 12, 855–859

Wang, Y., & Conlon, J.-M. (1995) Pept. 15, 603–606

Habu, A., Ohishi, T., Mihara, S., Ohkubo, R., Hong, Y., Mochizuki, T., and Yanaihara, N. (1994) Biomed. Res. 15, 357–361

Ahren, B., Rorswan, P., and Berggren, P (1988) FEBS Lett 229, 233–237

Davis, T.-M., Burrin, J.-M, and Bloom, S.-R (1987) J. Clin. Endocr. Metab. 65, 1248–1252

Bek, T., Ottesen, B., and Fahrenkug, J. (1988) Peptides 9, 497–500

Ottlez, A., Snyder, G., and Mccann, S.-M. (1988) Proc. Natl. Acad. Sci. USA 85, 9861–9865

Murakami, Y., Kato, Y., Koshiyama, H., Inoue, t., Yanaihara, N., & Imura, H. (1987) eur. J. Pharmacol. 136, 415–418

Pramanik, A., & Ogren, S.-O. (1993) Reg. Pept.

Fisone, G., & Consolo, S. (1987) Proc Natl. Acad. Sci. USA 84, 7339–7343

Crawley, J.-N. (1993) Behav. Brain Res. 57, 133–141

Ogren, S.-O., Hokfelt, T., Kask, K., Langel, U., & Bartfai, T. (1992) Neurosci. 51, 1–5

Crawley, J.-N., & Wenk, G.-L. (1989) Trends Neurosci. 12, 278–282

Crawley, J. N. (1996) Life Sciences 58, 2185–2199

Kaplan, L. M., Gabriel, S. M., Koening, J. I., Sundey, M. E., Spindel, E. R., Martin, J. B., & Chin, W. W. (1988) Proc. Natl. Acad. Sci. USA 85, 7408–7412

Zhang, X., Verge, V. M. K., Wiesenfeld-Hallin, Z., Piehl, & Hoekfelt, T. (1993) EXp. Brain Res. 93, 450–461

Hoekfelt, T., Zhang, X., & Wiesenfeld-Hallin, Z. (1994) Trends Neursci. 17, 22–30

Israel, D.-I. (1993) Nucl. Acids Res. 21, 2627–263

Current Protocols in Molecular Biology (1994) eds. Ausubel, F.-M., Brent, R., Kingston, R.-E., Moore, D.-D., Seidman, J.-G., Smith, J.-A., Struhl, K. (John Wiley & Sons, Inc.)

Craxton, M. (1991) Methods: A Companion to Methods in Enzymology 3, 20–24

Chirgwin, J.-M., Przybyla, A.-E., McDonald, R.-J., & Rutter, W.-J. (1979) Biochemistry 18, 5294–5299

Nordeen, S.-K. (1988) Biotechniques 6, 454–5299
Chen, C., & Okayama, H. (1987) Mol. Cell. Biol. 7, 2745–2752
Dignam, J.-D., Lebovitz, r.-M., & Roeder, R.-G. (1983) Nucleic Acids Res. 11, 1475–1489
Kofler, B. Liu, M., Jacoby, A., Shine, J., & Iismaa, T. (1996) Gene 182, , 71–75
Kofler, B., Evans, H., Liu, M., Falls, V., Ismaa, T., Shine, J., & Herzog, H. (1995) DNA and Cell Biol. 14, 321–329.
Rokeus, A., & Washek, J. (1994) DNA and Cell Biol. 8, 845–855
Anouar, Y., MacArthur, L., Cohen, J., Iacangelo, A.-L., & Eiden, L.-E. (1994) J. Biol. Chem. 269, 6823–6831
Kaplan, L. M., Hoot, S.C., Abraczinskas, D. R., Strauss, R. M., Davidson, M. B., Hsu, D. W., & Koening, J. I. (1991) in Galanin: A Multifunctional Peptide in the Neuro-Endocrine System, eds. Hokfelt, T., Bartifai, T., Jacabowitz, D. (McMillan Press, London), pp. 43–64.
Xu, Z.-Q., Shi, T.-J., & Hoekfelt, T. (1996) Proc. Natl. Acad Sci. USA 93, 14901–14905
Giorgi, S., Fortoni, G., Baldi, G., & Cansolo, S. (1995) Eur. J. Neurosci. 7, 944–950
Planas, B., Kolb, P.-E., Raskind, M.-A., & Miller, M. (1997) J. Comp. Neurol. 379, 563–570
Kerekes, N., Landry, M., Rydhrinder, M., & Hoekfelt, T. (1997) Brain Res. 754, 131–141
Zhang, J., Pettersson, R., & Hoekfelt, T. (1996) Regul. Pept. 66, 179–189
Missale, C., Boroni, F., Sigala, S. , Zanellato, A., Toso, R.-D., Balsari, A., & Spano, P. (1994) Endocrinology 135, 290–298
Borrelli, E., Sawchenko, P., & Evans, R. (1992) Proc. Natl. Acad. Sci. USA 89, 2764–2768
Patterson, J.-C., & Childs, G. (1994) Endocrinology 135, 1689–1704
Day, R.-N., Koike, S., Sakai, M., Muramatsu, M., & Maurer, R.-A. (1990) Mol. Endocrinol. 4, 1964–1971
Nowakowski, B.-E., & Maurer, R.-A. (1994) Mol. Endocrinol. 8, 1742–1749
Nachtigal, M.-W, Nicke, B.-E., & Cattini, P.-A. (1992) J. Bio. Chem. 268, 8473–8479
Jackson, S.-M., Keech, C.-A., Williamson, D.-J., & Gutierrez-Hartmann, A. (1992) Mol. Cellular Bio. 12, 2708–2719
Kraner, S.-D., Chong, J.-A., Tsay, H., & Mandel, G. (1992) Neuron 9, 37–44
Jessel, T. M. In Principles of Neural Science. Elsevier New York. 258–269 (1991).
Hendry, I. A. In development, Regeneration and plasticity of the autonomic nervous system. Harwood Acadenie Publishers, Chur. 415–462 (1992).
Zigmond, R E. Neuroscientist. 3: 176–185 (1997)
Ma, W and Bisby, M A, Neuroscience. 79: 1183–1195 (1997)
Zhang, X. et al., Exp. Brain Res. 93: 459–561 (1993)
Hoekfelt, T. et al. TINS. 17: 22–30 (1994)
Villar, M J et al, Neuroscience. 33: 587–604 (1989)
Merchenthaler, I. et al, Crit. Rev. Neurobiol. 7: 229–274 (1993)
Bartfai, T. et al. Crit. Rev. Neurobiol. 7: 229–274 (1993)
Vrontakis, M. E., et al, J. Inv. Endocr. 14: 785–794 (1991)
Hoekfelt, T. et al., Neurosci. Lett. 83: 217–220 (1987)
Kashiba, H. et al. Brain Res. 582: 47–57 (1.992)
Vilar, J. J. et al. Exp. Neurol. 112: 29–39 (1991)
Unemoto, S. et al Mol. Brain Res. 23: 93–99 (1994)
Arvidsson, J. et al, Neuroreport. 5: 1269–1272 (1994)
Herdegen, T. et al. Mol. Brai. Res. 17: 147–154 (1993)
Moore, R Y, et al. J. Comp. Neurol. 282: 512–522 (1989)
Rutharfurd, D. D. et al, Mol. Brain Res. 14: 261–266 (1992)
Saika, T., et al Mol. Brain Res. 11: 187–196 (1991)
Dagerlind, A. et al Neuroscience. 69: 1019–1023 (1995)
Mohney, R P, et al. J. Neurobiol. 25: 108–118 (1994)
Rao, M S, et al. Neuron. 11: 1175–1185 (1993)
Schreiber, R C et al Neuroscience 60: 17–27 (1994)
Post, C et al, Acta. Phys. Scand. 132: 583–584 (1988)
Wiesenfield-Halin, Z. et al PNAS 87: 7105–7109 (1990)
Wiesenfield-Halin, Z. et al PNAS 89: 3334–3337 (1992)
Verge, V M et al. Neurosci. Lett. 149: 193–198 (1993)
Ji, R R et al. PNAS 91: 12540–12543 (1994)
Wang, S. et al. Mol. Pharmacol. 52: 337–343 (1997)
Parker, E M et al. Mol. Brain Res. 34: 179–189 (1995)
Burgerin, M. C. et al J. Mol. Neurosci. 6:33–41 (1995)
Howard, A D, et al. FEBS-Lett. 405: 285–290 (1997)
Sullivan, K A, et al. Bioch. Bioph. Res. Com. 233: 823–828 (1997)
Habert-Ortoli, E. et al. PNAS 91: 9780–9783 (1994)
Gustafson, E L, et al NeuroReport. 7: 953–957 (1996)
Xu, Z Q et al, NeuroReport. 8: 237–242 (1996)
Simoneaux, D K et al., Mammalian Genome. 8: 875–878 (1997)
Xu, Z Q et al. PNAS 93: 14901–14905 (1996)
Vrontakis, M E et al. J.Biol.Chem. 262: 16755–16758 (1987)
Burke and Olson, "Preparation of Clone Libraries in Yeast Artificial-Chromosome Vectors" in *Methods in Enzymology*, Vol., 194, "Guide to Yeast Genetics and Molecular Biology", eds. C. Guthrie and G. Fink, Academic Press, Inc., Chap. 17, pp. 251–270 (1991).
Capecchi, "Altering the genome by homologous recombination" *Science* 244:1288–1292 (1989).
Davies et al., "Targeted alterations in yeast artificial chromosomes for inter-species gene transfer", *Nucleic Acids Research*, Vol. 20, No. 11, pp. 2693–2698 (1992).
Dickinson et al., "High frequency gene targeting using insertional vectors", *Human Molecular Genetics*, Vol. 2, No. 8, pp. 1299–1302 (1993).
Duff and Lincoln, "Insertion of a pathogenic mutation into a yeast artificial chromosome containing the human APP gene and expression in ES cells", *Research Advances in Alzheimer's Disease and Related Disorders*, 1995.
Huxley et al., "The human HPRT gene on a yeast artificial chromosome is functional when transferred to mouse cells by cell fusion", *Genomics*, 9:742–750 (1991).
Jakobovits et al., "Germ-line transmission and expression of a human-derived yeast artificial chromosome", *Nature*, Vol. 362, pp. 255–261 (1993).
Lamb et al., "Introduction and expression of the 400 kilobase precursor amyloid protein gene in transgenic mice", *Nature Genetics*, Vol. 5, pp. 22–29 (1993).
Pearson and Choi, Expression of the human $-amyloid precursor protein gene from a heast artificial chromosome in transgenic mice. Proc. Natl. Scad. Sci. USA, 1993. 90:10578–82.
Rothstein, "Targeting, disruption, replacement, and allele rescue: integrative DNA transformation in yeast" in *Methods in Enzymology*, Vol. 194, "Guide to Yeast Genetics and Molecular Biology", eds. C. Guthrie and G. Fink, Academic Press, Inc., Chap. 19, pp. 281–301 (1991).
Schedl et al., "A yeast artificial chromosome covering the tyrosinase gene confers copy number-dependent expression in transgenic mice", *Nature*, Vol. 362, pp. 258–261 (1993).
Strauss et al., "Germ line transmission of a yeast artificial chromosome spanning the murine", (I) collagen locus", *Science*, Vol. 259, pp. 1904–1907 (1993).
Gordon, 1989, ATransgenic Animals@, *Intl. Rev. Cytol.*, 115:171–229.
Lavitrano et al, 1989, ASperm Cells as Vectors for Introducing Foreign DNA into Eggs: Genetic Transformation of Mice@ *Cell* 57:717–723
Lo, 1983, ATransformation by Iontophoretic Microinjection of DNA Multiple Integrations Without Tandem Insertions@, *Mol. Cell. Biol* 3(10):1803–1814
Thompson et al, 1989, AGerm Line Transmission and Expression of a Corrected HPRT Gene Produced by Gene Targeting in Embryonic Stem Cells@, *Cell* 56:313–321
Van der Putten et al, 1985, AEfficient insertion of genes into the mouse germ line via retroviral vectors@, PNAS USA 82:6148–6152.

```
Untitled Sequence # 2 ->Full Restriction Map
DNA sequence    187 b.p.    CAGCTGTGCTTT . . . ATTTATTATAAG    linear
Positions of Restriction Endonucleases sites (unique sites underlined)

Alu I
Pyu II                      BsmA I
NapB II       Mae I    Bsr I        Fnu4H I       Mae III     Rsa I
| |            |         |            |             |           |
CAGCTGTGCTTTCTAGGCACACACTGGTGTCTCTGCGGCACTCCCCCGTTACCCCCTGTACTCTGGCAACT GCCACCCC   8
GTCGACACGAAAGATCCGTGTGTGACCACAGAGACGCCGTGAGGGGGCAATGGGGGGACATGAGACCGTTGA CGGTGGGG
| |      ·    |    ·    |      |·     |        ·        |·           |·      ·       ·
1           13       23        35           48          59
1                              29
2

Msp I
                                                            Hga I
                        Nai I                               Aha II
                        SfaN I
               Mse I   SfaN I           Mae I           Mse I      Hpa II
                 |      || |              |               |          | |
TACACTTTGTCCTAATAAAATTAAGATGCATCATATCACTCTGCTAGACATCTTTTTTTTTTTAAGGCGTCC GGTTTTTT   1
ATGTGAAACAGGATTATTTTAATTCTACGTAGTATAGTGAGACGATCTGTAGAAAAAAAAAAAATTCCGCAGG CCAAAAAA
       ·|      ·      || ·        ·      ·     ·          ·       ·   || ·|   ·
             101      108        124              142         151
                      105                                     146
                      106                                     147
                                                                     151

TTTTTAGATTTATTTATTTATTATAAG 187
AAAAATCTAAATAAATAAATAATATTC
            ·         ·

Restriction Endonucleases site usage
Aat II      -        BstN I      -       HinC II     -       Ple I      -
Acc I       -        BstU I      -       HinD III    -       Pml I      -
Afl II      -        BstX I      -       Hinf I      -       PpuM I     -
Afl III     -        BstY I      -       HinP I      -       Pst I      -
Aha II      1        Bsu36 I     -       Hpa I       -       Pvu I      -
Ala I       1        Cfr10 I     -       Hpa II      1       Pvu II     1
Alw I       -        Cla I       -       Hph I       -       Rsa I      1
AlwN I      -        Dde I       -       Kpn I       -       Rsr II     -
Apa I       -        Dpn I       -       Mae I       2       Sac I      -
ApaL I      -        Dra I       -       Mae II      -       Sac II     -
Ase I       -        Dra III     -       Mae III     1       Sal I      -
Asp718      -        Drd I       -       Mbo I       -       Sau3A I    -
Ava I       -        Dsa I       -       Mbo II      -       Sau96 I    -
Ava II      -        Eae I       -       Mlu I       -       Sca I      -
Avr II      -        Eag I       -       Mme I       -       ScrF I     -
BamH I      -        Ear I       -       Mnl I       -       Sec I      -
Ban I       -        Eco47 III   -       Msc I       -       SfaN I     2
Ban II      -        Eco57 I     -       Mse I       2       Sfi I      -
Bbe I       -        EcoN I      -       Msp I       1       Sma I      -
Bbv I       -        EcoO109 I   -       Nae I       -       SnaB I     -
Bbv II      -        EcoR I      -       Nar I       -       Spe I      -
Bcl I       -        EcoR II     -       Nci I       -       Sph I      -
Bcn I       -        EcoR V      -       Nco I       -       Spl I      -
Bgl I       -        Esp I       -       Nde I       -       Ssp I      -
Bgl II      -        Fnu4H I     1       Nhe I       -       Stu I      -
BsaA I      -        Fok I       -       Nla III     -       Sty I      -
Bsm I       -        Fsp I       -       Nla IV      -       Taq I      -
BsmA I      1        Gdi II      -       Not I       -       Tth111 I   -
Bsp1286 I   -        Csu I       -       Nru I       -       Tth111 II  -
BspH I      -        Hae I       -       Nsi I       1       Xba I      -
BspM I      -        Hae II      -       Nsp7524 I   -       Xca I      -
BspM II     -        Hae III     -       NspB II     1       Xho I      -
Bsr I       1        Hga I       1       NspH I      -       Xcm I      -
BssH II     -        HciA I      -       PaeR7 I     -       Xma I      -
BstB I      -        HgiE II     -       PflM I      -       Xmn I      -
BstE II     -        Hha I       -

Untitled Sequence # 1 -> I    Restriction Map
DNA sequence    325 b.p.    GGTACCCTGCCA . . . AGCACCCTCGAG    linear
Positions of Restriction Endonucleases sites (unique sites underlined)
```

-continued

```
                                                                    Sau3A I
                                                                    Mbo I
  Rsa I                      Hif I                                  Dpn I
  Nla IV                     ScrF I                                 BstY I
  Kpn I                      Ecor II                                Bgl II
  Ban I                      BstN I                        Dde I
  Asp718                     Sec I                         BsmA I   Alu I
   ||                         ||  |                          |      |  | ||
GGTACCCTGCCAGAGTATCCTACCCCTGGATTCAAAAATACTCTCAAAAGGACACATTGGGTGGTCTCTGTA GCTGAGAT 80
CCATGGGACGGTCTCATAGGATGGGGACCTAAGTTTTTATGAGAGTTTTCCTGTGTAACCCACCAGAGACAT CGACTCTA
   ||        .          ||  | .           .          .     |      .| | ||  .
   1         24             25                              64     72
   1                        25                                     74
   1                        25                                            77
   1                        25                                            77
   2                        29                                            78
                                                                          78
                                                                          78

Sau3A I
                                              Mbo I     Mae III
       Mae III      Dde I       Fnu4H I       Dpn I     Mae II
          |           |           |             |         | |
CTTGCGTGACCATTGCCCATAAACCTGAGCAAAGGCGGCGGTGGAAAGGTAAGATCAGGGACGTGACCGCAG GAGAGCAG 160
GAACGCACTGGTAACGGGTATTTGGACTCGTTTCCGCCGCCACCTTTCCATTCTAGTCCCTGCACTGGCGTC CTCTCGTC
          |    .      |     .     |     .     .         |    .| |      .
          86         105         115                     133  141
                                                         133
                                                         133          143

BstU I          Alu I                                  Gsu I
    Hga I           Mnl I                        Alu I     Nla IV    Nla III
    | |              | |                           |       | |         |
TGGGGACGCGATGTGTGGGAGGAGCTTCTAAATTATCCATCAGCACAAGCTGTCAGTGGCTCCAGCCATGAA TAAATGTA 240
ACCCCTGCGCTACACACCCTCCTCGAAGATTTAATAGGTAGTCGTGTTCGACAGTCACCGAGGTCGGTACTT ATTTACAT
    | |     .      |  |    .         .          |        | |       .
    165            179                           208      218       227
      167             183                                   220

Sau96 I
                                                Nla III Tth111 I    Xho I
                                                Sph I     Ava II    PaeR7 I
               Sty I                            NspH I      Nla IV  Ava I
               Sec I     Mnl I                  Nsp7524 I           Mnl I
       Nla IV            Taq I                   ||      |||          ||
          |              |  |
TAGGGAAAGGCAGGAGCCTTGGGGTCGAGGAAAACAGGTAGGGTATAAAAAGGGCATGCAAGGGACCAAGTC CAGCACCC 320
ATCCCTTTCCGTCCTCGGAACCCCAGCTCCTTTTGTCCATCCCATATTTTTCCCGTACGTTCCCTGGTTCAG GTCGTGGG
          .    | |       | |       .          .        ||      .|||      .  ||
          253                                           294     302         319
                 257       265                          294       303       320
                 257          267                       294       304       320
                                                          295       303     320
                                                                303

Taq I
|
TCGAG 325
AGCTC
|
321
```

Restriction Endonucleaaes site usage

| | | | | | | | |
|---|---|---|---|---|---|---|---|
| Aat II | - | BstN I | 1 | HinC II | - | Ple I | - |
| Acc I | - | BstU I | 1 | HinD III | - | Pml I | - |
| Afl II | - | BstX I | - | Hinf I | 1 | PpuM I | - |
| Afl III | - | BstY I | 1 | HinP I | - | Pst I | - |
| Aha II | - | Bsu36 I | - | Hpa I | - | Pvu I | - |
| Alu I | 3 | Cfr10 I | - | Hpa II | - | Pvu II | - |
| Alw I | - | Cla I | - | Mph I | - | Rsa I | 1 |
| AlwN I | - | Dde I | 2 | Kpn I | 1 | Rsr II | - |
| Apa I | - | Dpn I | 2 | Mae I | - | Sac I | - |

-continued

```
Rat Gel cDNA # 1 -> Full Restreiction Map
DNA sequence   680 b.p.   ccctacgccgct ... aaactagcaagt   linear
Positions of Restriction Endonucleases sites (unique sites underlined)

∞Sau3AI
                 ∞MboI
                 DpnII                        AciI
                 DpnI                         ∞HinP1I
                 MspAlI    NlaIII             HhaI
                 AciI      ∞HinP1I     MnlI   Cac8I         ScrFI              Sau96I
                 BsoFI     HhaI        MwoI   BstUI         BstNI    BsmAI     AvaII
                 ||        |           |      ||||          |        |         |
        ccctacgccgctgatctgcgccatgcagtgagcgaccctcgcgcccgccactctacgccacgcctggacgga gacacttg 80
        gggatgcggcgactagacgcggtacgtcactcgctgggagcgcgggcggtgagatgcggtgcggacctgcct ctgtgaac
                 ||  •    |  •|        •|     | ||||         •         •|        |
                 7        18           32     40             63        71       80
                 8        18              37 43              63                  80
                          22               41
                                           41
                    13
                    13                      45
                    13
                    13

ScrFI                 ScrFI
                              NlaIV        BstNI                 BstNI
                              MspI         BsaJI                 BfaI
                              HpaII        HaeIII                ∞NheI
              BsgI            ScrFI        MscI    BsoFI         MwoI
              BspMI   ∞AluI   NciI         EaeI    BbvI          Cac8I    NlaIV
              | |    |        |||          |||     |             ||        |
        gacctgcactaaccagctacgcccggttcccaccactgctcaagatggccaggggcagcgttatcctgctag cctggctc 160
        ctggacgtgattggtcgatgcgggccaaggggtggtgacgagttctaccggtccccgtcgcaataggacgatc ggaccgag
              | |    •|       •|||         ||  |             ||•  |         •
              82     95       102          126  135           148  156
              84              102          126  135           148
                              103          127                148
                              103          129                149
                                105        129                     153
                                                                   153

Cac8I
                                                                           ∞HinPlI
                           AvaI                                            HhaI
                           MwoI     SfaNI              MnlI    Sau96I      ∞HaeII
                           Bsp1286I                    MboII   NlaIV
                   BslI    BanII    FokI               EarI    AvaII       ∞Eco47III
                   |       |||      ||                 |       |           |||
        ctgttggttgcaaccctgtcagccactctgggctcgggatgccaacaaaggagaagagaggctggaccctg aacagcgc 240
        gacaaccaacgttgggacagtcggtgagacccgagcccctacggttgttcctcttctctccgacctgggac ttgtcgcg
                   •       •|||     ||•              •    |•        ||    •
                           183      191              214      225          236
                                    191              214      225          236
                                    193              219      225          237
                                    194                                    237
                                                                           239

Sau96I
         HaeIII
         Sau96I
         NlaIV                                            MnlI
         Bsp1286I              ∞Sau3AI                    MwoI
         Bsp120I               ∞MboI                      BglI
         BanII                 DpnII                      HaeIII
         ApaI     NlaIII       DpnI         NlaIII                    MnlI
         ||       |            |            |    |||                  |
        tggctaccttctgggcccacatgccattgacaaccacagatcatttagcgacaagcatggcctcacaggcaa gagggagt 320
        accgatggaagacccgggtgtacggtaactgttggtgtctagtaaatcgctgttcgtaccggagtgtccgtt ctccctca
         •||      |            |•           •    |•||                •|
         253      260          279          296                      313
         253                   279          299
         253                   279          300
         253                                300
         253                                301
         253
         254
         254
```

-continued

```
                    BfaI          ∞RsaI
     BsrI    MnlI   BsmAI         Csp6I       DdeI              AciI
      |      |      | |            |           |                 | |
     accatggaagtggaggaagggagactaggaaaaaatttaccc ctgcctgagagcaatatcgtccgctaaaaa aaaaaaaa  4(
     cggtgaccttcacctccttccctctgatccttaaaaaatggg gacggactctcgttatagcaggcgaaaaaa aaaaaaaa
      | •   | •   | | •   | •    | •           | •|               •
     325   335   343                   362    372                338
                       347                                        
                             362                                  391
```

```
                                        Sau96I
                                        HaeIII
                                        Sau96I
                                        NlaIV
                                        ∞EcoO109I
                                        Bsp1286I
                                        Bsp120I
                                        BanII
                                        ApaI
                                        NlaIV
                                        ScrFI
                                        NciI
                                        MspI
                                        HpaII
                                        BsaJI                                          HaeIII
                        MseI                              ScrFI              ∞StyI
                        HaeIII         TagI               BstNI              BsaJI              MboII
             ∞EcoNI  MnlI            MnlI   MwoI                             MscI         DdeI
      DdeI   BslI   ∞EcoO109I   BglI  Cac8I    FokI    EaeI      MnlI        MnlI         BbsI
       |      | |    | | |   | | |    | •|     | •|    | •|      | •|      • | |            |
     aagtttctcagtttcttgcaccttaaagaggccggggccctcgacagcctgcctggcatcccccttggccacc tcctcaga  4{
     cccaaagagtcaaagaacgtggaatttctccggccccgggagctgtcggacggaccgtaggggaaccggtgg aggagtct
       | •    • | |    | | |    | | |    | •|    | •|    | •|    • | |        •
     407    421   428   434           447    456    465    471           479
                  421         430     439    447    457    465    474
                        423           441           
                              432                                 475
                              432                          462                 479
                              432                   452    462
                              432                   452           466
                              432
                              434
                              435
                              435
                              435
                              435
                              435
                              435
                              435
                              436
                              436
```

```
                    Bsp1286I
         BsmAI     BsiHKAI           MseI
         BsaI      ∞ApaLI           ∞DraI
BfaI    DdeI       Alw44I   MnlI   Tsp509I    BfaI
 |       ||          |       |      | ||       |
acacctagagcagtcctgagaccacacccactgtgcacctgtgtcctctgctataatttaaagtcattctag gctaaaaa 56
actggatctcgtcaggactctggtgtgggtgacacgtggacacaggagacgatattaaatttcagtaagatc cgatttttt
 |    •  ||   •    |    •    |    •    | ||   •    |    •    |    •
485    496        513        525       535        549
       498        513                  537
       498        513                  538
                  513

MboII
         AciI                                DdeI      MseI
 MnfI   AciI    MnlI              MwoI   SfaNI      Tsp509I
  |      |      |                   |     |  |      | |
aaaatcttccgccaactcctcaagccaacactttgttctctgcctttgatgctgagttattacaattaagat gttttgatt 6
aaatagaaggcggttgaggagttcggttgtgaaacaagagacggaaactacgactcaataatgttaattcta caaaactaa
  |      | •    |  •      •          • |    •|  •      ||  •      •
  1     568    577                   601   607       623           caaaactaa
  1                                        611       625
564

Tsp509I   Tsp45I      BfaI
          |        |          |
aaaagtaattatattgtgtgacataataaaaactagcaagt 680
aaatcattaatataacacactgtattattttgatcgttca
          |   •    |   •     |     •
         646      657       672

Restriction Endonucleases site usage
atII          -     ∞BsiWI    -     ∞Eco47III   1     ∞NsiI     -
ccI           -     BslI      2     Eco57I      -     PacI      -
iI            4     BsmAI     3     ∞EcoNT      1     PaeR7I    -
```

What is claimed is:

1. A transgenic mouse having integrated in its genome a nucleic acid construct comprising a mammalian pituitary specific promoter operably linked to a galanin cDNA sequence wherein said mouse expresses galanin in the pituitary at an elevated level compared to a non-transgenic mouse and further wherein galanin is secreted into the circulation at an elevated level compared to a non-transgenic mouse, such that said mouse develops pituitary adenomas.

2. The transgenic mouse according to claim 1, wherein said galanin cDNA is selected from the group consisting of rat and human cDNA according to SEQ ID NO: 1–3.

3. A construct comprising galanin cDNA operably linked to a pituitary specific promoter.

4. The construct according to claim 3, wherein said galanin cDNA is rat or human cDNA.

5. A method of making a transgenic mouse whose genome comprises a nucleic acid construct wherein the construct comprises a mammalian pituitary specific promoter operably linked to a galanin cDNA sequence, said method comprising the steps of: transferring a nucleic acid construct comprising a mammalian pituitary specific promoter operably linked to a zalanin cDNA sequence to a murine zygote; allowing said zygote to develop to term; obtaining a mouse whose genome comprises the nucleic acid construct; breeding said mouse with a non-transgenic mouse to obtain $F_1$ offspring and selecting a mouse whose zenome comprises the nucleic acid construct, wherein said mouse expresses galanin in the pituitary at an elevated level compared to a non-transgenic mouse and further wherein galanin is secreted into the circulation at an elevated level compared to a non-transgenic mouse, such that said mouse develops pituitary adenomas.

* * * * *

SEQUENCE LISTING

<160> NUMBER OF SEQ ID NOS: 8

<210> SEQ ID NO 1
<211> LENGTH: 187
<212> TYPE: DNA
<213> ORGANISM: Homo sapiens

<400> SEQUENCE: 1
cagctgtgct ttctaggcac acactggtgt ctctgcggca ctcccccgtt acccccctgt      60
actctggcaa ctgccacccc tacactttgt cctaataaaa ttaagatgca tcatatcact     120
ctgctagaca tctttttttt tttaaggcgt ccggtttttt tttttagatt tatttattta     180
ttataag                                                                187

<210> SEQ ID NO 2
<211> LENGTH: 325
<212> TYPE: DNA
<213> ORGANISM: rat

<400> SEQUENCE: 2
ggtaccctgc cagagtatcc taccoctgga ttcaaaaata ctctcaaaag gacacattgg      60
gtggtctctg tagctgagat cttgcgtgac cattgcccat aaacctgagc aaaggcggcg     120
gtggaaaggt aagatcaggg acgtgaccgc aggagagcag tggggacgcg atgtgtggga     180
ggagcttcta aattatccat cagcacaagc tgtcagtggc tccagccatg aataaatgta     240
```

| | |
|---|---|
| tagggaaagg caggagcctt ggggtcgagg aaaacaggta gggtataaaa agggcatgca | 300 |
| agggaccaag tccagcaccc tcgag | 325 |

<210> SEQ ID NO 3
<211> LENGTH: 680
<212> TYPE: DNA
<213> ORGANISM: rat

<400> SEQUENCE: 3

| | |
|---|---|
| ccctacgccg ctgatctgcg ccatgcagtg agcgaccctc gcgcccgcca ctctacgcca | 60 |
| cgcctggacg gagacacttg gacctgcact aaccagctac gcccggttcc caccactgct | 120 |
| caagatggcc aggggcagcg ttatcctgct agcctggctc ctgttggttg caaccctgtc | 180 |
| agccactctg gggctcggga tgccaacaaa ggagaagaga ggctggaccc tgaacagcgc | 240 |
| tggctacctt ctgggcccac atgccattga caaccacaga tcatttagcg acaagcatgg | 300 |
| cctcacaggc aagagggagt taccactgga agtggaggaa gggagactag gaagtgttgc | 360 |
| tgtaccoctg cctgagagca atatcgtccg cactataatg gagtttctca gtttcttgca | 420 |
| ccttaaagag gccggggccc tcgacagcct gcctggcatc cccttggcca cctcctcaga | 480 |
| agacctagag cagtcctgag accacaccca ctgtgcacct gtgtcctctg ctataattta | 540 |
| aagtcattct aggctaaaaa gaatcttccg ccaactcctc aagccaacac tttgttctct | 600 |
| gcctttgatg ctgagttatt acaattaaga tgttttgatt ggagtaatta tattgtgtga | 660 |
| cataataaaa actagcaagt | 680 |

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 4

| | |
|---|---|
| gccatgcagt gagcgaccc | 19 |

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 5

| | |
|---|---|
| gcatcccgag ccccagagtg | 20 |

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 6

| | |
|---|---|
| cctggacgga gacacttgga cctgc | 25 |

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: primer

```
<400> SEQUENCE: 7
agggtcgtca ctgcatggc                                                 19

<210> SEQ ID NO 8
<211> LENGTH: 1584
<212> TYPE: DNA
<213> ORGANISM: MOUSE

<400> SEQUENCE: 8
ggatcccaga tgggtcttag gagaagaggg ggacaacttg gctcagggtc atgcagtgtt      60
catcaggaca ttggttagcc cgagtgactg tggtctcttg tgatccgctg ctccttgctc    120
cagcaacgga gtcatgttaa gccgtgatca gaaccctctt gggtgaacaa ggctcctcag    180
gacctgggtc accatgctag tggggttcac ttctgggcca ggtgacagag tgctcctgat    240
gagccccaaa ggctaaacacg ttcatcagag ctgcgccctg gttaaatatc tcacgctttg    300
ggagtccgga gttgctagct ctgtgtctgt cctgaggtga gatttcaggg tacctgtatg    360
ctgatgtgct gctcctgcac aggttggcta aactccctgg gtgcagacag ctctgcacct    420
tggcaagaat ctggcctggg gctctgcagg actcaaccac agtcacgaca gagaccactc    480
cagaaacggg gctctaaggg aaaatggatg gttggggcac agctgccagc caccctctac    540
ccagccctca gccctgaatg gctgcacccc tccccctttt tccccagcaa aagaggaatg    600
gaggaccctg gaccagggta gggaagctgc agtaacatgg tgcaaagcag tcctgggaat    660
ttggtttctc aggaggtgtc cgtgactggc cttgcttggg ctttggggtg gtccattcca    720
gccccagccc tgggaaggag agcaagacct cctcgccagc ctcaggatgg gggtgtcggg    780
gactcattct tgtgtgagta cggggcagaa cagtgggaag tgactctgtg atgcagggtt    840
ggccgggaga tagtctggga ctgtgggtgg tcctctcctg agcccagga gcgggagcgg      900 gttccggtca cagcggccct tgggactcgc aggaggcggc gctgagcggg tgacgcggca    960
gctcccaccg ggtataaatc gcggcagcag cgcggctcct gcggcggaca cgtcgaggga   1020
tcctcgtgcg cttccctacg ccgctgatct gcgccatgca gtgagcgacc ctcgcgcccg   1080
ccactctacg ccacgcctgg acggagacac ttggacctgc actaaccagc tacgcccggt   1140
tcccaccact gctcaaggta cccgcgtccc accgaggctt gcctggccct agtcctcctg   1200
cggtttgtag ccccatccct gccctgcac ccctcacagc tgtgttccca tcacccagcc    1260
actcccatgc caatgccttc gcagtccaag tgccccagac atgtgcgtgt gcaggactgc   1320
tcaggtgcgt ccactcatcc acttctttcc ttccagatgg ccaggggcag cgttatcctg   1380
ctagcctggc tcctgttggt tgcaaccctg tcagccactc tggggctcgg gatgccagta   1440
agtactgggg acagctgact tgtaaagagg gctaaggggtg tcagatctga agatcagcct   1500
ggaagaagga tggttcattg tccccatagc aggaataggg tggggggaca tgtccctgaa   1560
gctgctggag ggtggggagg atcc                                          1584
```